United States Patent
Lee et al.

(10) Patent No.: US 11,038,116 B2
(45) Date of Patent: Jun. 15, 2021

(54) COMPOUND AND ORGANIC THIN FILM AND THIN FILM TRANSISTOR AND ELECTRONIC DEVICE

(71) Applicant: Samsung Electronics Co., Ltd., Suwon-si (KR)

(72) Inventors: Eunkyung Lee, Seoul (KR); Don-Wook Lee, Seoul (KR); Jeong Il Park, Seongnam-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 0 days.

(21) Appl. No.: 16/531,376

(22) Filed: Aug. 5, 2019

(65) Prior Publication Data
US 2020/0168806 A1 May 28, 2020

(30) Foreign Application Priority Data
Nov. 26, 2018 (KR) .................. 10-2018-0147721

(51) Int. Cl.
*H01L 51/00* (2006.01)
*C07D 517/22* (2006.01)
*C07D 517/04* (2006.01)
*H01L 51/05* (2006.01)

(52) U.S. Cl.
CPC ........ *H01L 51/0071* (2013.01); *C07D 517/04* (2013.01); *C07D 517/22* (2013.01); *H01L 51/0068* (2013.01); *H01L 51/0545* (2013.01); *H01L 51/0558* (2013.01)

(58) Field of Classification Search
CPC .................. C07D 517/04; C07D 517/22
See application file for complete search history.

(56) References Cited

U.S. PATENT DOCUMENTS

| | | | |
|---|---|---|---|
| 7,816,673 B2 | 10/2010 | Park et al. | |
| 8,124,964 B2 | 2/2012 | Takimiya et al. | |
| 8,138,355 B2 | 3/2012 | Watanabe | |
| 8,232,546 B2 | 7/2012 | Takimiya et al. | |
| 8,816,100 B2 | 8/2014 | Takimiya | |
| 9,318,713 B2 | 4/2016 | Park et al. | |
| 9,537,102 B2 | 1/2017 | Park et al. | |
| 9,853,225 B2 | 12/2017 | Takeya et al. | |
| 10,056,563 B2 | 8/2018 | Miyazaki et al. | |
| 2011/0224445 A1 | 9/2011 | Takimiya | |
| 2016/0226005 A1 | 8/2016 | Park et al. | |
| 2019/0112319 A1 | 4/2019 | Lee et al. | |

FOREIGN PATENT DOCUMENTS

| | | | |
|---|---|---|---|
| EP | 1932847 A1 | 6/2008 | |
| EP | 3228622 A2 | 10/2017 | |
| EP | 3228622 A3 | 11/2017 | |
| JP | 2007-122029 A | 5/2007 | |
| JP | 2009267134 A | 11/2009 | |
| JP | 2010-177642 A | 8/2010 | |
| KR | 10-2011-0075024 A | 7/2011 | |
| KR | 10-2012-0078051 A | 7/2012 | |
| KR | 10-2015-0056051 A | 5/2015 | |
| WO | WO-08026602 A1 | 3/2008 | |
| WO | WO-20090009790 A1 | 1/2009 | |
| WO | WO-2012-118174 A1 | 9/2012 | |
| WO | WO-14136827 A1 | 9/2014 | |

OTHER PUBLICATIONS

Extended European Search Report for corresponding Application No. 19205425.2, dated Feb. 26, 2020.
Julien Bonnamour et al, Iron(III) Triflate as a Catalyst for the Synthesis of Indoles by Intramolecular C—H Amination, Organic Letters, vol. 13, No. 8, Mar. 11, 2011, pp. 2012-2014.
Database Beaxys, Database accession No. 7140240, 7141170, 7142484 (XRN); & Kamat; Gadaginamath Indian Journal of Chemistry—Section B Organic and Medicinal Chemistry, Jan. 30, 2020, vo. 33, 1994, pp. 255-259.
Database Beaxys, Database accession No. 4488284, 4543171(XBN); & Plattner; Parks J. Heterocycl. Chem., Jan. 30, 2020, vol. 20, 1983, pp. 1059-1062.
Database Beaxys, Database accession No. 1252625 (XBN); & Demebseman et al. Bulletin De La Societe Chimique De France 1965, 1473-1486, Jan. 30, 2020.

*Primary Examiner* — Noble E Jarrell
(74) *Attorney, Agent, or Firm* — Harness, Dickey & Pierce, P.L.C.

(57) ABSTRACT

Disclosed are a compound represented by Chemical Formula 1A or 1B, an organic thin film including the same, a thin film transistor, and an electronic device.

[Chemical Formula 1A]

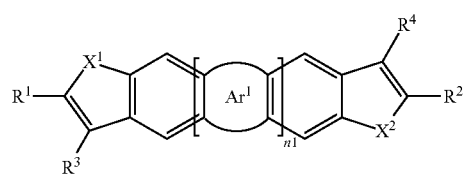

[Chemical Formula 1B]

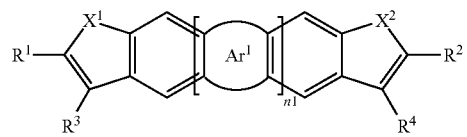

In Chemical Formula 1A or 1B, $X^1$, $X^2$, $Ar^1$, $R^1$ to $R^4$, and $n_1$ are the same as described in the detailed description.

31 Claims, 5 Drawing Sheets

COMPOUND AND ORGANIC THIN FILM AND THIN FILM TRANSISTOR AND ELECTRONIC DEVICE

CROSS-REFERENCE TO RELATED APPLICATION

This application claims priority to and the benefit of Korean Patent Application No. 10-2018-0147721 filed in the Korean Intellectual Property Office on Nov. 26, 2018, the entire contents of which are incorporated herein by reference.

BACKGROUND

1. Field

A compound, an organic thin film, a thin film transistor, and an electronic device are disclosed.

2. Description of Related Art

A flat panel display such as a liquid crystal display (LCD) or an organic light emitting diode (OLED) display includes a thin film transistor (TFT) that is a three-terminal element as a switch. Researches on an organic thin film transistor (OTFT) including an organic semiconductor such as a small molecular semiconductor or polymer semiconductor instead of an inorganic semiconductor such as a silicon (Si) semiconductor as one kind of the thin film transistor are being actively conducted.

The organic thin film transistor may be made into a fiber or a film due to characteristics of an organic material, and thus is drawing attention as a core element for a flexible display device. The organic thin film transistor may be manufactured using a solution process such as inkjet printing, and may be easily applied to a large area flat panel display where a deposition process has a limit.

SUMMARY

An embodiment provides a compound applicable to an electronic device such as a thin film transistor.

Another embodiment provides an organic thin film including the compound.

Yet another embodiment provides a thin film transistor including the compound.

Still another embodiment provides an electronic device including the compound or the thin film transistor.

According to one embodiment, a compound represented by Chemical Formula 1A or 1B is provided.

[Chemical Formula 1A]

[Chemical Formula 1B]

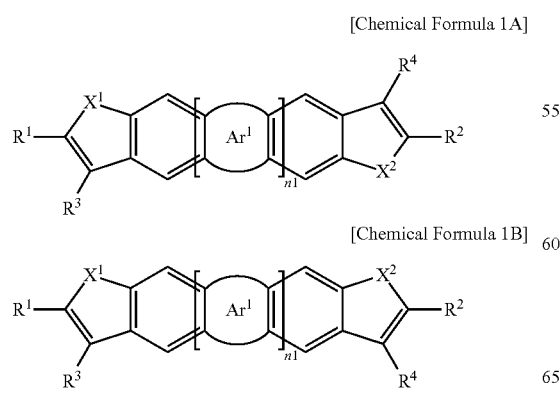

In Chemical Formula 1A or 1B, $X^1$ and $X^2$ are different from each other and are independently O, S, Se, Te, or $NR^a$, $Ar^1$ is at least one substituted or unsubstituted benzene, at least one substituted or unsubstituted furan, at least one substituted or unsubstituted thiophene, at least one substituted or unsubstituted selenophene, at least one substituted or unsubstituted tellurophene, or a fused ring of two or more of the foregoing groups, $R^1$ and $R^2$ are different from each other or $R^3$ and $R^4$ are different from each other, $R^1$ to $R^4$ and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is 0 or 1.

One of $X^1$ and $X^2$ may be Se or Te.

In some embodiments, $Ar^1$ may include at least one of a substituted or unsubstituted furan, a substituted or unsubstituted thiophene, substituted or unsubstituted selenophene, and substituted or unsubstituted tellurophene.

In some embodiments, $Ar^1$ may include a structure represented by a substituted or unsubstituted group listed in Group 1.

[Group 1]

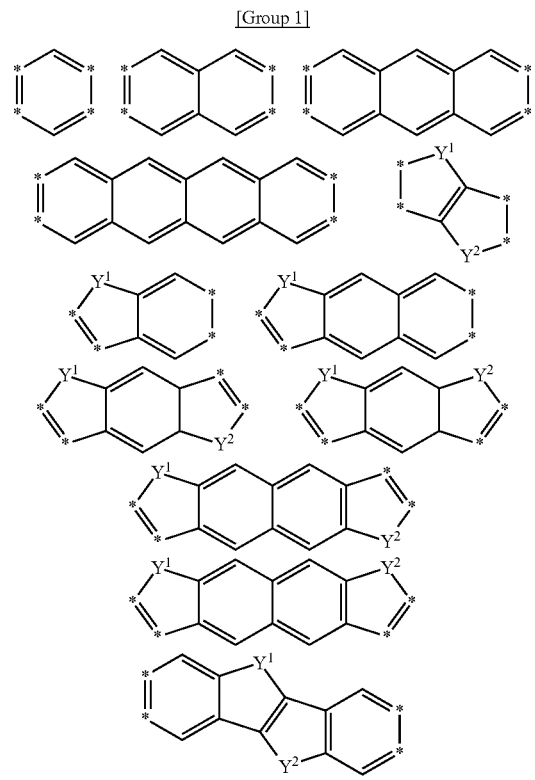

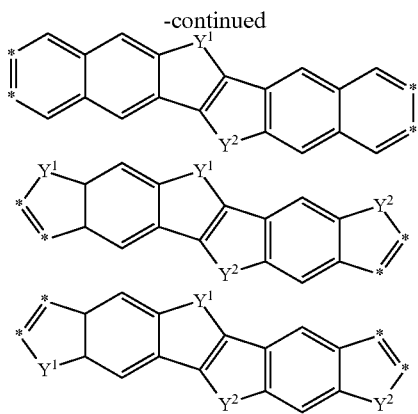

In Group 1,

Y$^1$ and Y$^2$ are independently one of O, S, Se, and Te, and

* is a linking point with Chemical Formula 1A or 1B.

At least one of X$^1$ and X$^2$ of Chemical Formula 1A or 1B may be different from Y$^1$ and Y$^2$ listed in Group 1, respectively.

One of X$^1$ and X$^2$ may be Se or Te, and Y$^1$ and Y$^2$ may independently be O or S.

In some embodiments, one of R$^1$ and R$^2$ may be hydrogen and the other of R$^1$ and R$^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

In some embodiments, one of R$^1$ and R$^2$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of R$^1$ and R$^2$ may be a substituted or unsubstituted C4 to C30 branched alkyl group, a substituted or unsubstituted C4 to C30 branched alkenyl group, a substituted or unsubstituted C4 to C30 branched alkynyl group, or a combination thereof.

In some embodiments, one of R$^1$ and R$^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of R$^1$ and R$^2$ may be a substituted or unsubstituted C3 to C30 cycloalkyl group, a substituted or unsubstituted C3 to C30 cycloalkenyl group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, or a combination thereof.

In some embodiments, one of R$^1$ and R$^2$ may be a substituted or unsubstituted C3 to C30 cycloalkyl group, a substituted or unsubstituted C3 to C30 cycloalkenyl group, a substituted or unsubstituted C6 to C30 aryl group, or a combination thereof and the other of R$^1$ and R$^2$ may be a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

In some embodiments, one of R$^1$ and R$^2$ may include a structure represented by one of Chemical Formulae 2A to 2C.

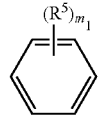

[Chemical Formula 2A]

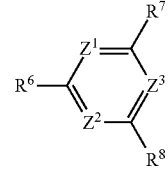

[Chemical Formula 2B]

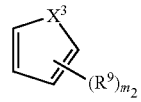

[Chemical Formula 2C]

In Chemical Formula 2A, 2B, or 2C,

Z$^1$ to Z$^3$ are independently N or CR$^b$, one of Z$^1$ to Z$^3$ is N,

X$^3$ is O, S, Se, Te, NR$^c$, CR$^d$R$^e$, or SiR$^f$R$^g$, m1 is an integer ranging from 0 to 5, m2 is an integer ranging from 0 to 3, R$^5$ to R$^9$ and R$^b$ to R$^g$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof or a linking point with Chemical Formula 1A or 1B, when R$^5$ is two or more, each R$^5$ may be the same or different and two adjacent R$^5$'s may be present independently or linked with each other to form a ring, and when R$^9$ is two or more, each R$^9$ may be the same or different and two adjacent R$^9$'s may be present independently or linked with each other to form a ring.

In some embodiments, one of X$^1$ and X$^2$ may be Se or Te, one of R$^1$ and R$^2$ may be hydrogen and the other of R$^1$ and R$^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

In some embodiments, one of $X^1$ and $X^2$ may be Se or Te, one of $R^1$ and $R^2$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and the other of $R^1$ and $R^2$ may be a substituted or unsubstituted C4 to C30 branched alkyl group, a substituted or unsubstituted C4 to C30 branched alkenyl group, a substituted or unsubstituted C4 to C30 branched alkynyl group, or a combination thereof.

In some embodiments, one of $X^1$ and $X^2$ may be Se or Te, one of $R^1$ and $R^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and the other of $R^1$ and $R^2$ may be a substituted or unsubstituted C3 to C30 cycloalkyl group, a substituted or unsubstituted C3 to C30 cycloalkenyl group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, or a combination thereof.

In some embodiments, one of $X^1$ and $X^2$ may be Se or Te, one of $R^1$ and $R^2$ may be a substituted or unsubstituted C3 to C30 cycloalkyl group, a substituted or unsubstituted C3 to C30 cycloalkenyl group, a substituted or unsubstituted C6 to C30 aryl group, or a combination thereof, and the other of $R^1$ and $R^2$ may be a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

According to another embodiment, an organic thin film including the compound is provided.

According to another embodiment, a thin film transistor includes a gate electrode, a source electrode and a drain electrode, and an organic semiconductor overlapping with the gate electrode. The source electrode and drain electrode may be electrically connected to the organic semiconductor wherein the organic semiconductor includes the compound represented by Chemical Formula 1A or 1B.

According to another embodiment, an electronic device includes the compound, the organic thin film or the thin film transistor.

Charge mobility of the compound may be improved.

DETAILED DESCRIPTION

Figure 1:
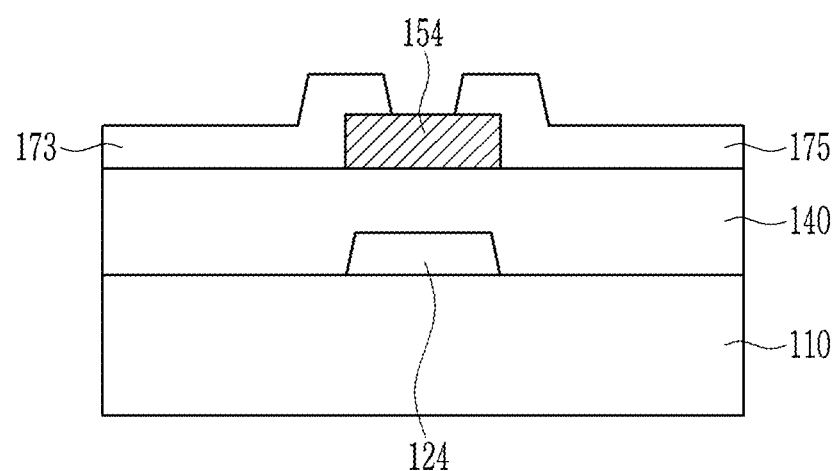
FIG. 1 is a cross-sectional view showing a thin film transistor according to an embodiment.

Example embodiments will hereinafter be described in detail, and may be easily performed by a person having an ordinary skill in the related art. However, this disclosure may be embodied in many different forms and is not to be construed as limited to the embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when a definition is not otherwise provided, "substituted" may refer to replacement of hydrogen of a compound by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heteroaryl group, a C3 to C30 heterocycloalkyl group, and a combination thereof.

As used herein, when a definition is not otherwise provided, "hetero" may refer to inclusion of one to four heteroatoms selected from N, O, S, Se, Te, Si, and P.

As used herein, when a definition is not otherwise provided, "alkyl group" may refer to a linear or branched, saturated, monovalent hydrocarbon group (e.g., a methyl group, an ethyl group, a propyl group, an isobutyl group, a sec-butyl group, a tert-butyl group, a pentyl group, an iso-amyl group, a hexyl group, etc.).

As used herein, when a definition is not otherwise provided, "alkenyl group" may refer to a linear or branched, saturated, monovalent hydrocarbon group (e.g., an ethenyl group) having at least one carbon-carbon double bond.

As used herein, when a definition is not otherwise provided, "alkynyl group" may refer to a linear or branched saturated monovalent hydrocarbon group including at least one carbon-carbon triple bond (e.g., an ethynyl group).

As used herein, when a definition is not otherwise provided, "alkoxy group" may refer to an aryl group that is linked via oxygen, for example a methoxy, an ethoxy, and a sec-butyloxy group.

As used herein, when a definition is not otherwise provided, "aryl group" may refer to a monovalent functional group formed by the removal of one hydrogen atom from one or more rings of an arene, e.g., phenyl or naphthyl. The arene may refer to a hydrocarbon having an aromatic ring, and includes monocyclic and polycyclic hydrocarbons, wherein the additional ring(s) of the polycyclic hydrocarbon may be aromatic or nonaromatic.

As used herein, when a definition is not otherwise provided, "arylalkyl group" may refer to an alkyl group where at least one hydrogen atom is replaced by an aryl group.

As used herein, when a definition is not otherwise provided, "alkylaryl group" may refer to an aryl group where at least one hydrogen atom is replaced by an alkyl group.

As used herein, when a definition is not otherwise provided, "aryloxy group" may refer to an aryl group that is linked via oxygen, and the aryl group is the same as described above.

As used herein, when a definition is not otherwise provided, "arylalkyl group" may refer to an aryl group where at least one hydrogen atom is replaced by a lower alkylene, e.g., methylene, ethylene, propylene, and the like. For example, the "arylalkyl group" may be a benzyl group or a phenylethyl group.

As used herein, when a definition is not otherwise provided, "cycloalkyl group" may refer to a monovalent functional group having one or more saturated rings in which all ring members are carbon, e.g., a cyclopentyl group and a cyclohexyl group.

As used herein, when a definition is not otherwise provided, "heteroalkyl group" may refer to the alkyl group defined above where methylene (—(CH)$_2$—) is replaced by —O—, —S—, —S($=$O)$_2$—, —Se—, or —NR— (wherein R is independently hydrogen or a C1 to C10 alkyl group).

As used herein, when a definition is not otherwise provided, "arylheteroalkyl group" may refer to the heteroalkyl group defined above where at least one hydrogen atom is replaced by an aryl group.

As used herein, when a definition is not otherwise provided, "heteroarylalkyl group" may refer to the alkyl group defined above where at least one hydrogen atom is replaced by a heteroaryl group.

As used herein, when a definition is not otherwise provided, "alkylheteroaryl group" may refer to the heteroaryl group defined above where at least one hydrogen atom is replaced by an alkyl group.

As used herein, when a definition is not otherwise provided, "aromatic ring" may refer to a functional group in which all atoms in the cyclic functional group have a p-orbital, and wherein these p-orbitals are conjugated. For example, the aromatic ring may be a C6 to C20 aryl group.

Expressions such as "at least one of," when preceding a list of elements (e.g., A, B, and C), modify the entire list of elements and do not modify the individual elements of the list. For example, "at least one of A, B, and C," "at least one of A, B, or C," "one of A, B, C, or a combination thereof," and "one of A, B, C, and a combination thereof," respectively, may be construed as covering any one of the following combinations: A; B; A and B; A and C; B and C; and A, B, and C."

Hereinafter, a compound according to an embodiment is described.

A compound according to an embodiment may be represented by Chemical Formula 1A or 1B.

[Chemical Formula 1A]

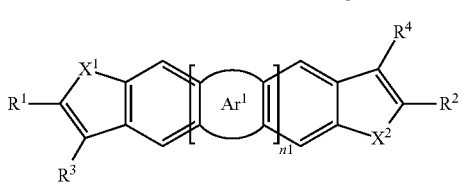

[Chemical Formula 1B]

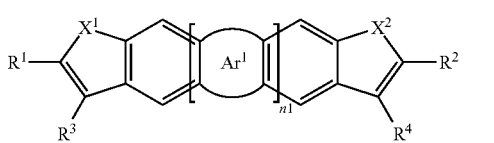

In Chemical Formula 1A or 1B, $X^1$ and $X^2$ are different from each other and are independently O, S, Se, Te, or NR$^a$, $Ar^1$ is at least one substituted or unsubstituted benzene, at least one substituted or unsubstituted furan, at least one substituted or unsubstituted thiophene, at least one substituted or unsubstituted selenophene, at least one substituted or unsubstituted tellurophene, or a fused ring of two or more of the foregoing, $R^1$ and $R^2$ are different from each other or $R^3$ and $R^4$ are different from each other, $R^1$ to $R^4$ and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is 0 or 1.

The compound is a condensed polycyclic aromatic compound including a condensed polycyclic aromatic ring having different heteroatoms as a core structure. The core structure has a benzo-heterocyclic ring, which is a fused ring of the pentagonal heterocyclic ring and the benzene ring at both ends, and the pentagonal heterocyclic rings are different from each other. That is, the compound may have an asymmetric core structure having different heterocyclic rings at both ends. Like this, the condensed polycyclic aromatic compound having an asymmetric core structure may have high crystallinity compared with the condensed polycyclic aromatic compound having a symmetrical core structure, thereby improving the charge mobility.

For example, one of $X^1$ and $X^2$ may be Se or Te.

For example, one of $X^1$ and $X^2$ may be Se and the other of $X^1$ and $X^2$ may be O, S, Te, or NR$^a$. For example, one of $X^1$ and $X^2$ may be Se and the other of $X^1$ and $X^2$ may be S or Te.

For example, one of $X^1$ and $X^2$ may be Te and the other of $X^1$ and $X^2$ may be O, S, Se, or NR$^a$. For example, one of $X^1$ and $X^2$ may be Te and the other of $X^1$ and $X^2$ may be S or Se.

For example, $Ar^1$ is a substituted or unsubstituted benzene; a substituted or unsubstituted furan; a substituted or unsubstituted thiophene; a substituted or unsubstituted selenophene; a substituted or unsubstituted tellurophene; a substituted or unsubstituted naphthalene; a substituted or unsubstituted anthracene; a substituted or unsubstituted tetracene; a fused ring of at least one substituted or unsubstituted benzene and at least one substituted or unsubstituted furan; a fused ring of at least one substituted or unsubstituted benzene and at least one substituted or unsubstituted thiophene; a fused ring of at least one substituted or unsubstituted benzene and at least one substituted or unsubstituted selenophene; a fused ring of at least one substituted or unsubstituted benzene and at least one substituted or unsubstituted tellurophene; a fused ring of at least two substituted or unsubstituted furans; a fused ring of at least two substituted or unsubstituted thiophenes; a fused ring of at least two substituted or unsubstituted selenophenes; a fused ring of at least two substituted or unsubstituted tellurophenes; a fused ring of at least one substituted or unsubstituted furan and at least one substituted or unsubstituted thiophene; a fused ring of at least one substituted or unsubstituted furan and at least one substituted or unsubstituted selenophene; a fused ring of at least one substituted or unsubstituted furan and at least one substituted or unsubstituted tellurophene; a fused ring of at least one substituted or unsubstituted thiophene and at least one substituted or unsubstituted selenophene; a fused ring of at least one substituted or unsubstituted thiophene and at least one substituted or unsubstituted tellurophene; or a fused ring of at least one substituted or unsubstituted selenophene and at least one substituted or unsubstituted tellurophene, but is not limited thereto.

For example, $n_1$ may be 0, and thus the compound may be a condensed polycyclic aromatic compound including a core structure of a condensed polycyclic aromatic ring in which four rings are fused.

For example, $n_1$ may be 1, and thus the compound may be a condensed polycyclic aromatic compound including a core structure of a condensed polycyclic aromatic ring in which five or more rings are fused. For example, the compound may be a condensed polycyclic aromatic compound including a core structure of a condensed polycyclic aromatic ring in which five to twelve rings are fused. For example, the compound may be a condensed polycyclic aromatic compound including a core structure of a condensed polycyclic aromatic ring in which six to ten rings are fused.

For example, $Ar^1$ may include one to eight rings, for example one to six rings.

For example, $Ar^1$ may be one of substituted or unsubstituted rings listed in Group 1.

[Group 1]

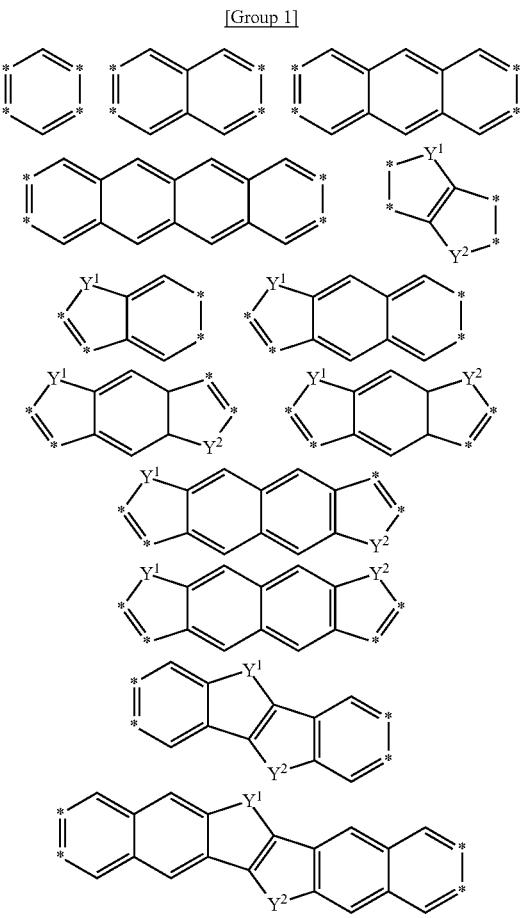
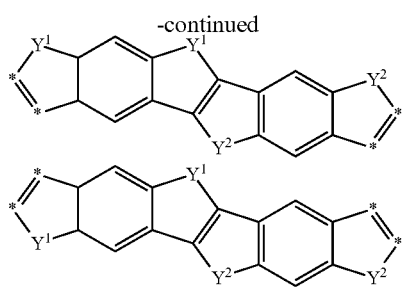

In Group 1,
$Y^1$ and $Y^2$ are independently one of O, S, Se, and Te, and * is a linking point with Chemical Formula 1A or 1B.

For example, in each ring of Group 1, $Y^1$ and $Y^2$ may be the same.

For example, $Y^1$ and $Y^2$ may independently be O.
For example, $Y^1$ and $Y^2$ may independently be S.
For example, $Y^1$ and $Y^2$ may independently be Se.
For example, $Y^1$ and $Y^2$ may independently be Te.
For example, in each ring of Group 1, $Y^1$ and $Y^2$ may be different from each other.

For example, one of $Y^1$ and $Y^2$ may be S and the other of $Y^1$ and $Y^2$ may be O.

For example, one of $Y^1$ and $Y^2$ may be 0 or S and the other of $Y^1$ and $Y^2$ may be Se or Te.

For example, one of $Y^1$ and $Y^2$ may be Se and the other of $Y^1$ and $Y^2$ may be Te.

For example, at least one of $X^1$ and $X^2$ of Chemical Formula 1A or 1B may be different from $Y^1$ and $Y^2$ of Group 1, respectively.

For example, one of $X^1$ and $X^2$ of Chemical Formula 1A or 1B may be Se or Te and $Y^1$ and $Y^2$ of Group 1 may independently be O or S.

For example, one of $X^1$ and $X^2$ of Chemical Formula 1A or 1B may be Se, the other of $X^1$ and $X^2$ may be O, S, Te or $NR^a$, and $Y^1$ and $Y^2$ of Group 1 may independently be O or S. For example, one of $X^1$ and $X^2$ of Chemical Formula 1A or 1B may be Se, the other of $X^1$ and $X^2$ may be S or Te, and $Y^1$ and $Y^2$ of Group 1 may independently be S.

For example, one of $X^1$ and $X^2$ of Chemical Formula 1 Å or 1B may be Te, the other of $X^1$ and $X^2$ may be O, S, Se, or $NR^a$, and $Y^1$ and $Y^2$ of Group 1 may independently be O or S. For example, one of $X^1$ and $X^2$ of Chemical Formula 1A or 1B may be Te, the other of $X^1$ and $X^2$ may be S or Se, and $Y^1$ and $Y^2$ of Group 1 may independently be S.

For example, one of $X^1$ and $X^2$ of Chemical Formula 1A or 1B may be Se, the other of $X^1$ and $X^2$ may be O, S, Te, or $NR^a$, and $Y^1$ and $Y^2$ of Group 1 may independently be Se or Te.

For example, one of $X^1$ and $X^2$ of Chemical Formula 1A or 1B may be Te, the other of $X^1$ and $X^2$ may be O, S, Se, or $NR^a$, and $Y^1$ and $Y^2$ of Group 1 may independently be Se or Te.

The compound may be a condensed polycyclic aromatic compound having a substituent that is positioned asymmetrically to the aforementioned asymmetric core structure. Herein, 'asymmetrically positioned' means that they do not have the same substituents at the positions corresponding to each other in the center of the fused polycyclic heteroaromatic ring.

For example, $R^1$ and $R^2$ of Chemical Formula 1A or 1B may be different from each other.

For example, $R^3$ and $R^4$ of Chemical Formula 1A or 1B may be different from each other.

For example, $R^1$ and $R^2$ of Chemical Formula 1A or 1B may be different from each other and $R^3$ and $R^4$ of Chemical Formula 1A or 1B may be the same.

For example, $R^3$ and $R^4$ of Chemical Formula 1A or 1B may be different from each other and $R^1$ and $R^2$ of Chemical Formula 1A or 1B may be the same.

For example, $R^1$ and $R^2$ of Chemical Formula 1A or 1B may be different from each other and $R^3$ and $R^4$ of Chemical Formula 1A or 1B may be different from each other.

The condensed polycyclic aromatic compound having an asymmetrically positioned substituent may exhibit liquid crystallinity in a desired (and/or alternatively predetermined) temperature range, and thus a degree of alignment of the molecules may be increased during heat treatment, and charge mobility of the organic thin film including the compound may be improved. The liquid crystallinity may be, for example, a smectic liquid crystallinity, and may be, for example, a smectic liquid crystallinity and a nematic liquid crystallinity. This liquid crystallinity is shown in a relatively low temperature range, and thus the process temperature may be lowered. For example, a temperature at which the compound exhibits liquid crystallinity may be less than or equal to about 400° C., for example about 150° C. to about 350° C., about 180° C. to about 300° C., or about 200° C. to about 280° C. In addition, additional annealing at a desired (and/or alternatively predetermined)temperature may further increase a degree of alignment of the molecules, thereby further improving charge mobility of the organic thin film including the compound.

For example, the compound may have a substituent at one side alone of the condensed polycyclic aromatic ring.

For example, one of $R^1$ and $R^2$ may be hydrogen and the other of $R^1$ and $R^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

For example, one of $R^3$ and $R^4$ may be hydrogen and the other of $R^3$ and $R^4$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

For example, the compound may have a linear substituent at one side of the condensed polycyclic aromatic ring and a non-linear substituent at the other side thereof.

For example, one of $R^1$ and $R^2$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of $R^1$ and $R^2$ may be a substituted or unsubstituted C4 to C30 branched alkyl group, a substituted or unsubstituted C4 to C30 branched alkenyl group, a substituted or unsubstituted C4 to C30 branched alkynyl group, or a combination thereof.

For example, one of $R^3$ and $R^4$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of $R^3$ and $R^4$ may be a substituted or unsubstituted C4 to C30 branched alkyl group, a substituted or unsubstituted C4 to C30 branched alkenyl group, a substituted or unsubstituted C4 to C30 branched alkynyl group, or a combination thereof.

For example, the compound may have a non-cyclic substituent at one side of the condensed polycyclic aromatic ring and a cyclic substituent at the other side thereof.

For example, one of $R^1$ and $R^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^1$ and $R^2$ may be a substituted or unsubstituted C3 to C30 cycloalkyl group, a substituted or unsubstituted C3 to C30 cycloalkenyl group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, or a combination thereof.

For example, one of $R^3$ and $R^4$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^3$ and $R^4$ may be a substituted or unsubstituted C3 to C30 cycloalkyl group, a substituted or unsubstituted C3 to C30 cycloalkenyl group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, or a combination thereof.

For example, the compound may have a cyclic substituent at one side of the condensed polycyclic aromatic ring and a heterocyclic substituent at the other side thereof.

For example, one of $R^1$ and $R^2$ may be a substituted or unsubstituted C3 to C30 cycloalkyl group, a substituted or unsubstituted C3 to C30 cycloalkenyl group, a substituted or unsubstituted C6 to C30 aryl group, or a combination thereof and the other of $R^1$ and $R^2$ may be a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

For example, one of $R^3$ and $R^4$ may be a substituted or unsubstituted C3 to C30 cycloalkyl group, a substituted or unsubstituted C3 to C30 cycloalkenyl group, a substituted or unsubstituted C6 to C30 aryl group, or a combination thereof and the other of $R^3$ and $R^4$ may be a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

For example, at least one of $R^1$ and $R^2$ may include a cyclic substituent or heterocyclic substituent and for example one of $R^1$ and $R^2$ may include a group represented by one of Chemical Formulae 2A to 2C.

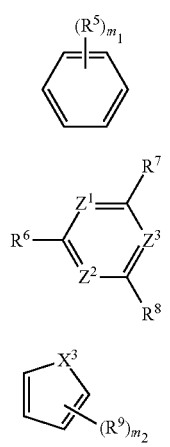

[Chemical Formula 2A]

[Chemical Formula 2B]

[Chemical Formula 2C]

In Chemical Formula 2A, 2B, or 2C,
$Z^1$ to $Z^3$ may independently be N or $CR^b$,
one of $Z^1$ to $Z^3$ may be N,
$X^3$ may be O, S, Se, Te, $NR^c$, $CR^dR^e$, or $SiR^fR^g$,
m1 may be an integer ranging from 0 to 5,
m2 may be an integer ranging from 0 to 3,
$R^5$ to $R^9$, and $R^b$ to $R^g$ may independently be hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof or a linking point with Chemical Formula 1A or 1B,
when $R^5$ is two or more, each $R^5$ may be the same or different and adjacent two $R^5$'s may independently be present or linked with each other to form a ring, and
when $R^9$ is two or more, each $R^9$ may be the same or different and adjacent two $R^9$'s may independently be present or linked with each other to form a ring.

For example, a group represented by Chemical Formula 2A may be an unsubstituted phenyl group or a phenyl group substituted with a C1 to C30 alkyl group.

For example, a group represented by Chemical Formula 2B may be a substituted or unsubstituted pyridinyl group, a substituted or unsubstituted pyrimidinyl group, or a substituted or unsubstituted triazinyl group.

For example, a group represented by Chemical Formula 2C may be a substituted or unsubstituted furanyl group, a substituted or unsubstituted thiophenyl group, a substituted or unsubstituted selenophenyl group, a substituted or unsubstituted tellurophenyl group, a substituted or unsubstituted pyrrolyl group, a substituted or unsubstituted cyclopentadienyl group, a substituted or unsubstituted silacyclopentadienyl group, or a combination thereof.

For example, at least one of $R^3$ and $R^4$ may include a cyclic substituent or heterocyclic substituent and for example one of $R^3$ and $R^4$ may include a group represented by one of Chemical Formulae 2A to 2C.

For example, $R^3$ and $R^4$ may independently hydrogen and the compound may be, for example, represented by Chemical Formula 1A-1 or 1B-1.

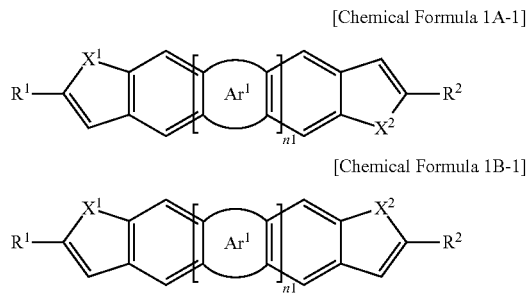

[Chemical Formula 1A-1]

[Chemical Formula 1B-1]

In Chemical Formula 1A-1 or 1B-1,
$X^1$, $X^2$, $Ar^1$, and $n_1$ are the same as described above, and
$R^1$ and $R^2$ may be different and may independently be hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

The compound may be for example one of compounds listed in Group 2, but is not limited thereto.

[Group 2]

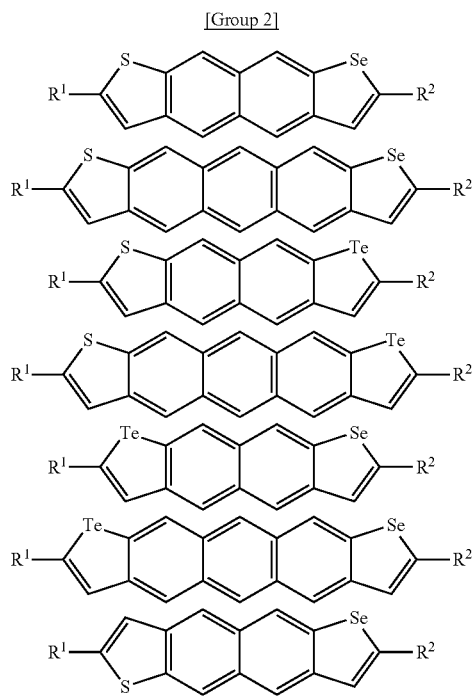

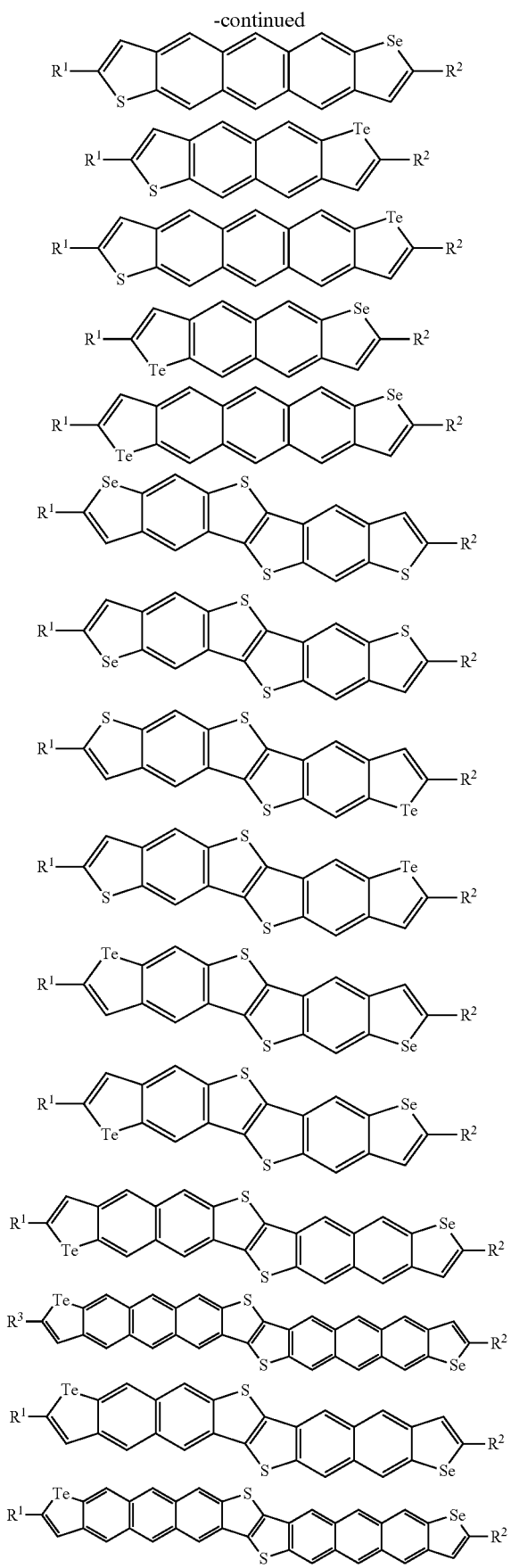
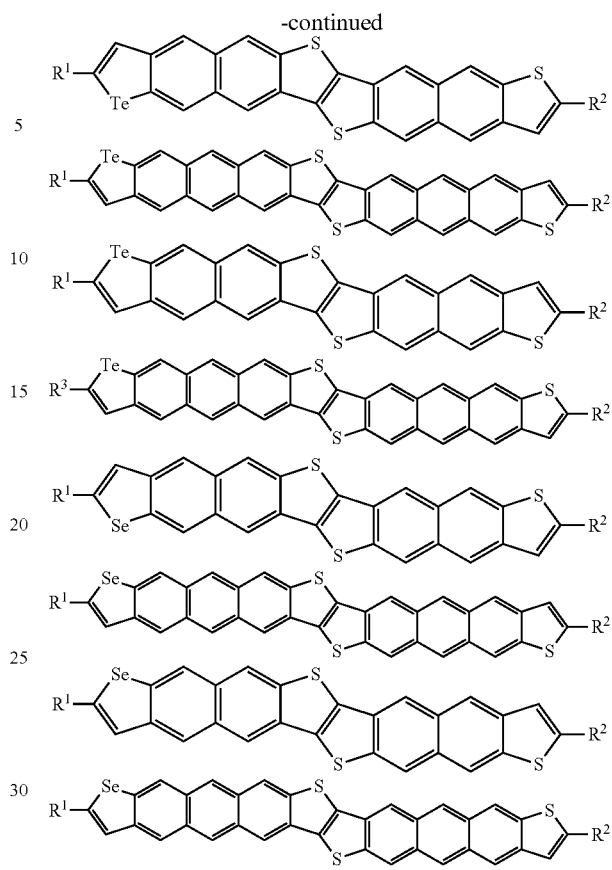
In Group 2, $R^1$ and $R^2$ are the same as described above. The compound may be, for example, one of compounds of Group 3, but is not limited thereto.
[Group 3]
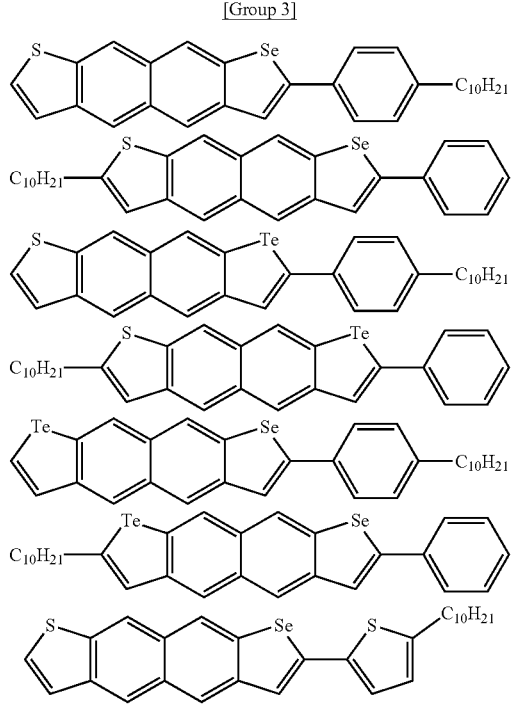

-continued
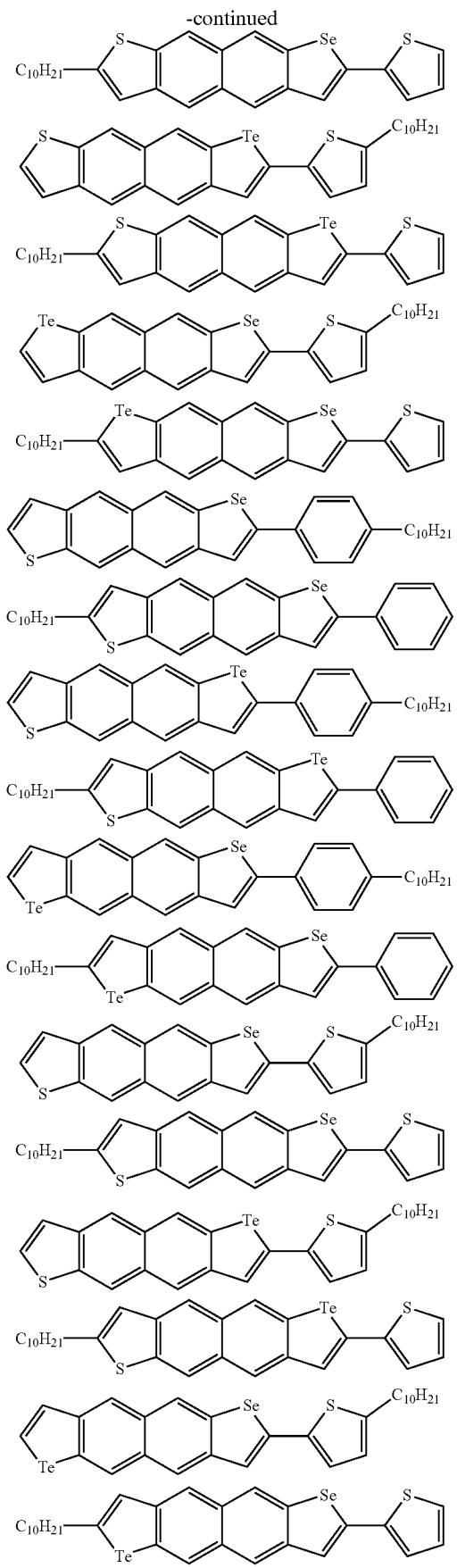
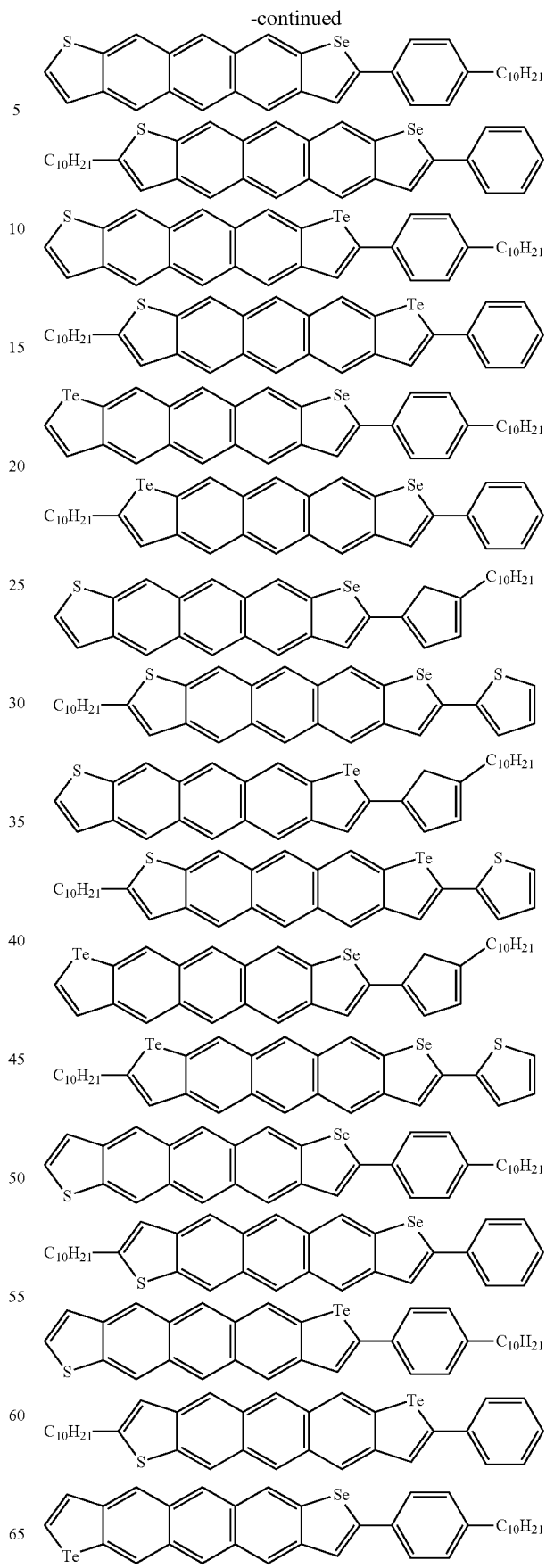

-continued
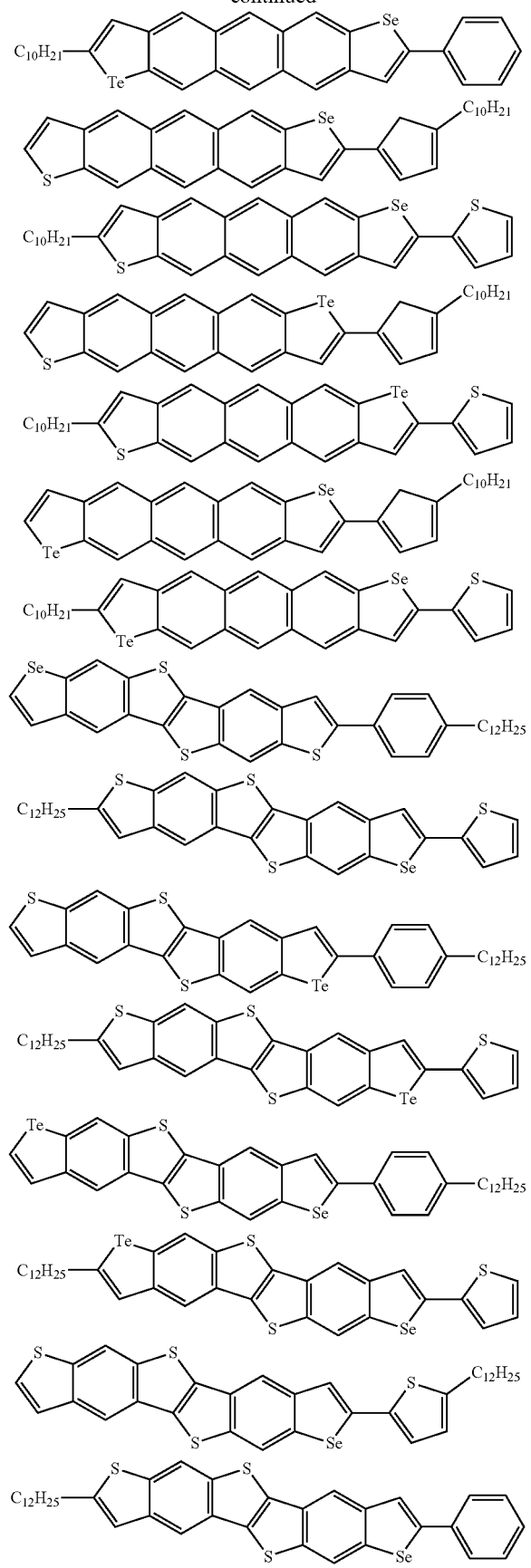
-continued
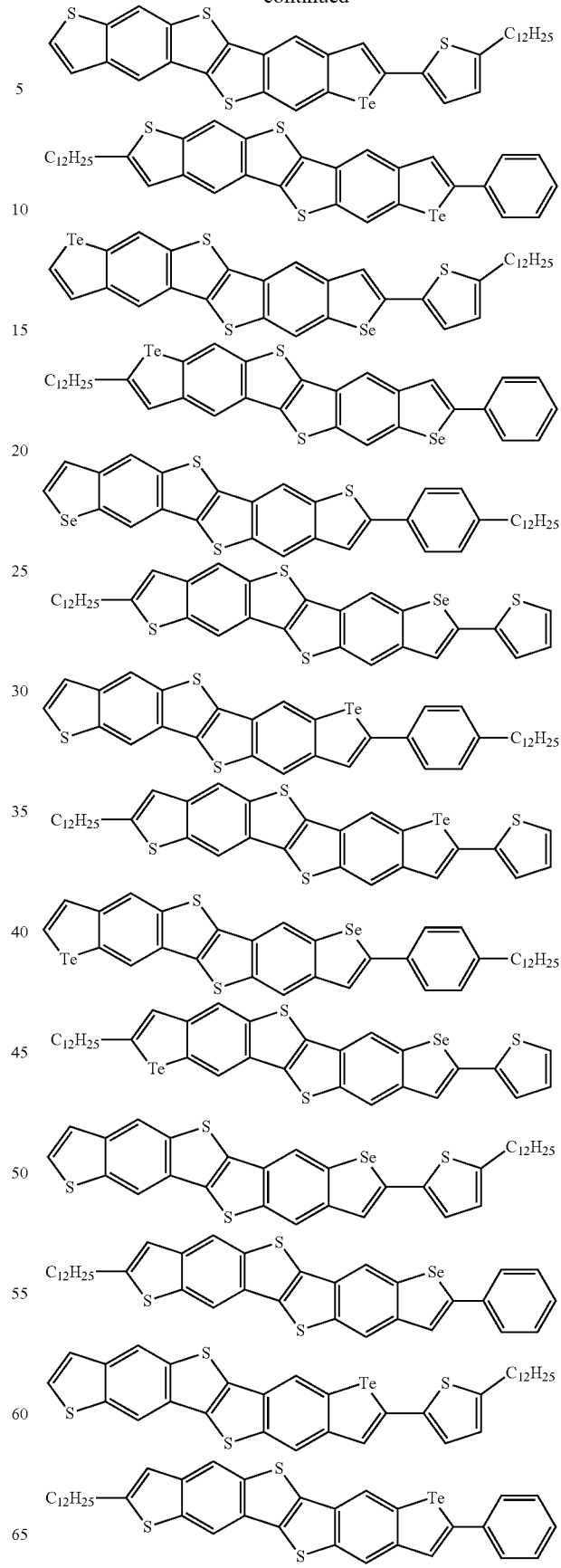

-continued

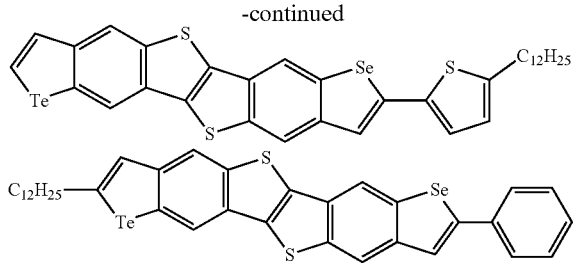

The aforementioned compound may be implemented into an organic thin film. The organic thin film may be a deposited thin film or a coating thin film formed by a solution process.

The organic thin film may be applied to various devices including an organic semiconductor. For example, the compound may be applied to a thin film transistor and may be applied to a charge transport layer and/or an active layer of an electronic device such as a solar cell, an organic light emitting diode (OLED) display, and an organic sensor.

Hereinafter, one example of a thin film transistor including the aforementioned compound is described referring to the drawing.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a cross-sectional view showing a thin film transistor according to an embodiment.

A gate electrode 124 is formed on a substrate 110 made of transparent glass, silicon, or plastic. The gate electrode 124 is connected to a gate line (not shown) transferring a gate signal. The gate electrode 124 may be made of a metal and/or metal alloy. For example, the gate electrode may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material and/or an inorganic material. Examples of the organic material may include a soluble polymer compound such as a polyvinyl alcohol-based compound, a polyimide-based compound, a polyacryl-based compound, a polystyrene-based compound, and benzocyclobutane (BCB), and examples of the inorganic material may include a silicon nitride (SiNx) and a silicon oxide (SiO2).

A source electrode 173 and a drain electrode 175 are formed on the gate insulating layer 140. The source electrode 173 and the drain electrode 175 face each other in the center of the gate electrode 124 therebetween. The source electrode 173 is electrically connected to the data line (not shown) transferring the data signal. The source electrode 173 and the drain electrode 175 may include at least one metal of gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may include the aforementioned compound. The organic semiconductor 154 may be formed in a solution process such as spin coating, slit coating, or inkjet printing by preparing the aforementioned compound in a form of a solution. However, the organic semiconductor 154 may be formed by vacuum-depositing or thermal evaporating the aforementioned compound.

Although FIG. 1 illustrates a bottom gate thin film transistor, inventive concepts are not limited thereto, and it may be applied to all thin film transistors such as a top gate structured thin film transistor.

The thin film transistor may be applied to a switch or driving device of various electronic devices, and the electronic device may include, for example, a liquid crystal display (LCD), an organic light emitting diode (OLED) display, an electrophoretic display, an organic photoelectric device, and an organic sensor, but is not limited thereto.

Hereinafter, the embodiments are illustrated in more detail with reference to examples. However, these examples are non-limiting, and inventive concepts are not limited thereto.

Synthesis of Compound

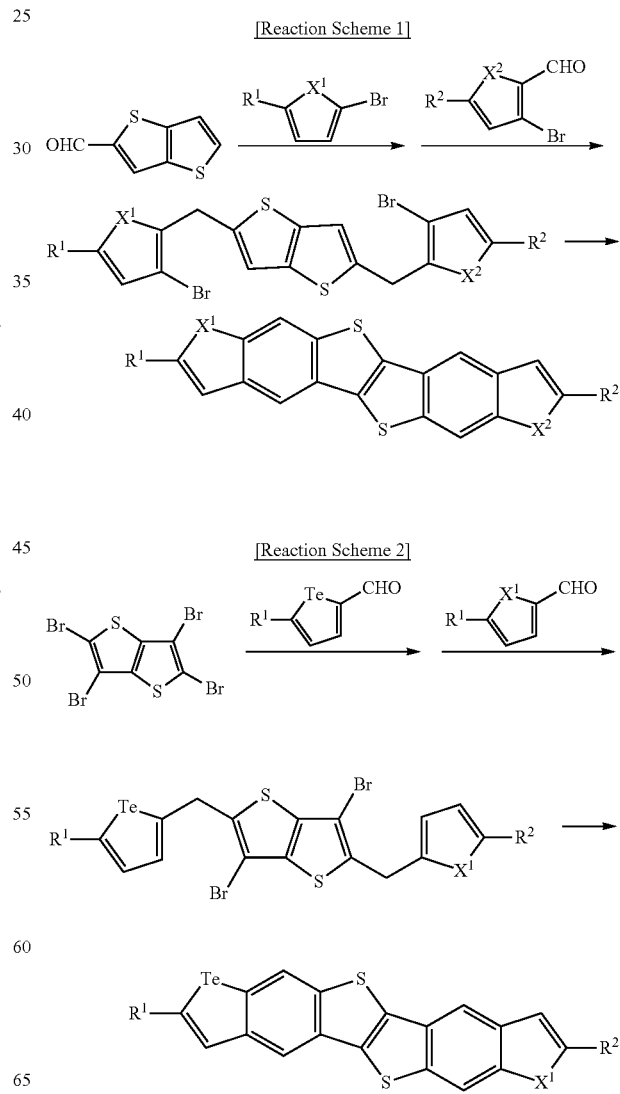

Synthesis Example 1
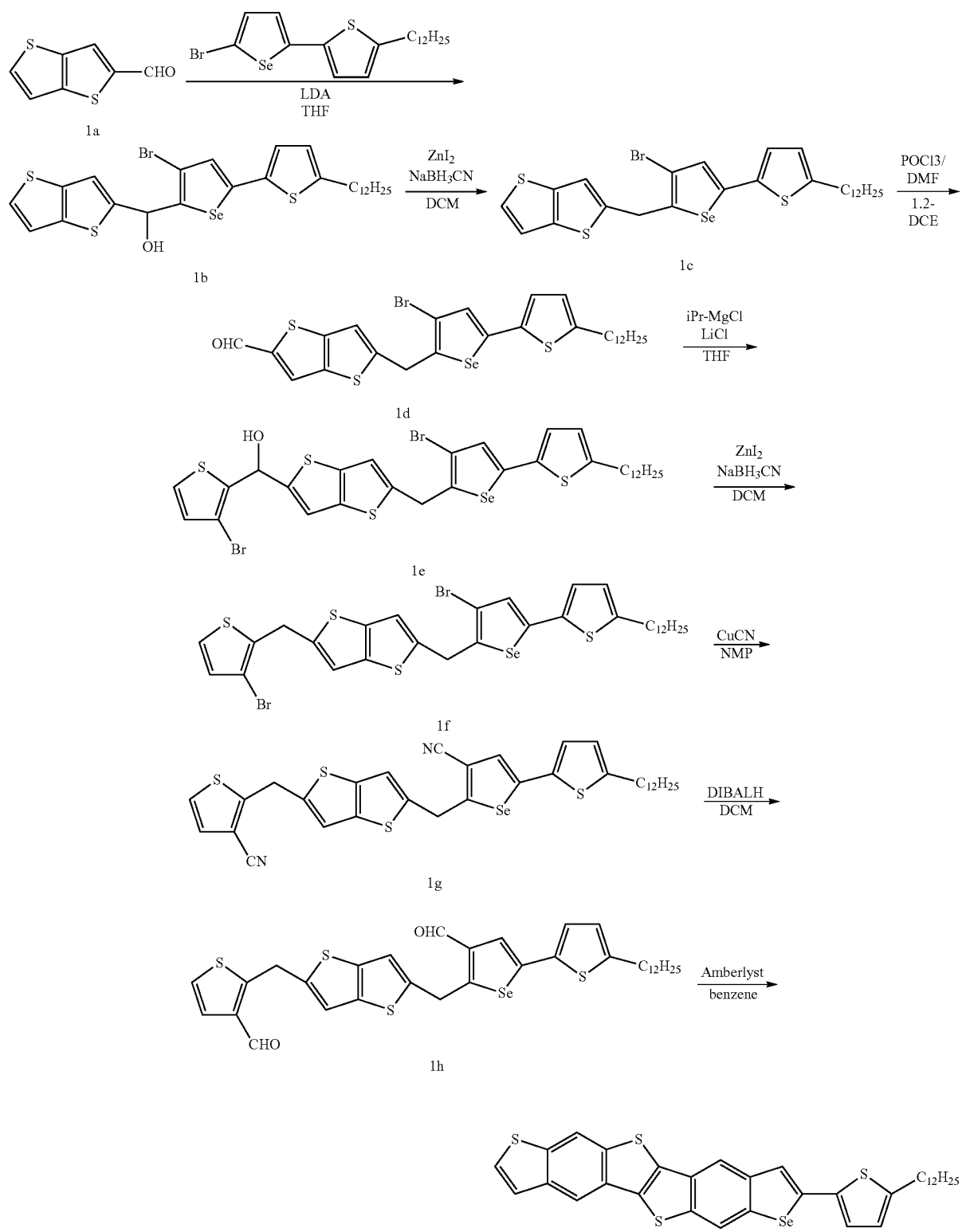

Synthesis of Compound 1b 2-(5-bromoselenophen-2-yl)-5-dodecylthiophene) (15 g, 32.58 mmol) is dissolved in 500 ml of tetrahydrofuran (THF) and then, cooled down to −78° C. Subsequently, lithium diisopropylamine (LDA, a 2.0 M solution in THF) (24.43 ml, 48.87 mmol) is added thereto, and the mixture is stirred for 2 hours. Next, Compound 1a (6.58 g, 39.1 mmol) is added thereto, and the obtained mixture is slowly heated up to room temperature and stirred for 12 hours. Then, 30 mL of an ammonium chloride saturated solution is added thereto, and the resultant is extracted with ethyl acetate and is several times washed with water. The extract is dried with subsequently magnesium sulfate, filtered, and then, after removing a solvent therefrom, purified through silica column chromatography to obtain Compound 1 b. Herein, a yield is 95%.

$^1$H NMR (500 MHz, CDCl$_3$): δ ppm 7.35 (d, 1H), 7.28 (s, 1H), 7.21 (s, 1H), 6.91 (d, 1H), 6.66 (d, 1H), 6.34 (d, 1H), 2.73 (t, 2H), 2.75 (s, 1H), 1.65 (t, 2H), 1.28 (m, 18H), 0.88 (t, 3H)

Synthesis of Compound 1c

Compound 1 b (19 g, 30.23 mmol) is dissolved in dimethylchloride and then, cooled down to 0° C. Next, zinc iodide (ZnI$_2$, 15.44 g, 48.36 mmol) and sodium cyanoborohydride (13.3 g, 211.58 mmol) are added thereto, and the obtained mixture is slowly heated up to room temperature and stirred for 12 hours. Subsequently, 30 mL of an ammonium chloride saturated solution is added thereto, and then, the resultant is extracted with dimethylchloride and is several times washed with water. Then, the extract is dried with magnesium sulfate, filtered, and after removing a solvent therefrom, purified through silica column chromatography to obtain Compound 1c. Herein, a yield is 99%.

$^1$H NMR (500 MHz, CDCl$_3$): δ ppm 7.32 (d, 1H), 7.19 (d, 1H), 7.12 (s, 1H), 7.08 (s, 1H), 6.84 (d, 1H), 6.63 (d, 1H), 4.36 (s, 2H), 2.75 (t, 2H), 1.65 (t, 2H), 1.29 (m, 18H),), 0.88 (t, 3H)

Synthesis of Compound 1d 1,2-dimethyl formamide (72.4 ml, 935. 34 mmol) is put in a 1 L flask and then, cooled down to 0° C. Next, phosphoryl chloride (43.7 ml, 31.18 mmol) is slowly added thereto, and the obtained mixture is stirred for 2 hours. Subsequently, a solution obtained by dissolving Compound 2c in 1,2-dichloroethane (1000 ml) is added thereto, and the obtained mixture is heated up to 100° C. After 2 hours, a 1N sodium hydroxide (NaOH) solution is added thereto to make it basified, and the resultant is extracted with chloroform. Then, the extract is dried with magnesium sulfate, filtered, and after removing a solvent therefrom, purified through silica column chromatography to obtain Compound 1d. Herein, a yield is 42%.

$^1$H NMR (500 MHz, CDCl$_3$): δ ppm 9.94 (s, 1H), 7.86 (s, 1H), 7.18 (s, 1H), 7.09 (s, 1H), 6.87 (d, 1H), 6.63 (d, 1H), 4.40 (s, 2H), 2.76 (t, 2H), 1.55 (t, 2H), 1.26 (m, 18H),), 0.87 (t, 3H)

Synthesis of Compound 1e 2,3-dibromothiophene (1.17 ml, 10.3 mmol) is added to tetrahydrofuran (THF, 100 ml) and then, cooled down to −78° C. Subsequently, an isopropyl magnesium chloride lithium chloride complex (5.15 ml, 10.3 mmol) is slowly added thereto, and the obtained mixture is slowly heated up to room temperature and cooled down to −78° C. again. Next, a solution obtained by dissolving Compound 1d (3.3 g, 5.15 mmol) in tetrahydrofuran (THF, 20 ml) is added thereto, and the obtained mixture is stirred for 1 hour. Then, 30 mL of an ammonium chloride saturated solution is added thereto, and the resultant is extracted with ethylacetate, and is several times washed with water. Then, the extract is dried with magnesium sulfate, filtered, and after removing a solvent therefrom, purified through silica column chromatography to obtain Compound 1e. Herein, a yield is 95%.

Synthesis of Compound 1f

Compound 1e (4.44 g, 5.52 mmol) is dissolved in dimethylchloride and cooled down to 0° C. Subsequently, zinc iodide (ZnI$_2$, 2.82 g, 8.84 mmol) and sodium cyanoborohydride (2.43 g, 28.67 mmol) are added thereto and then, slowly heated up to room temperature and stirred for 12 hours. Next, 30 mL of an ammonium chloride saturated solution is added thereto, and the resultant is extracted with dimethylchloride, and is several times washed with water. Subsequently, the extract is dried with magnesium sulfate, filtered, and after removing a solvent therefrom, purified through silica column chromatography to obtain Compound 1f. Herein, a yield is 87%.

$^1$H NMR (500 MHz, CDCl$_3$): δ ppm 7.18 (d, 1H), 7.06 (s, 1H), 7.03 (s, 1H), 7.00 (s, 1H), 6.94 (d, 1H), 6.83 (d, 1H), 6.63 (d, 1H), 4.33 (s, 2H), 4.32 (s, 2H), 2.74 (t, 2H), 1.64 (t, 2H), 1.29 (m, 18H),), 0.87 (t, 3H)

Synthesis of Compound 1g

Compound 1f (4.6 g, 5.8 mmol) is added to N-methyl pyrrolidone (69 ml), and copper cyanide (CuCN, 2.1 g, 23.36 mmol) is added thereto. The obtained mixture is put in a microwave device and reacted at 180° C. for 2 hours. Subsequently, the resultant is added to a 1 N hydrochloric acid (HCl) solution and then, stirred for 30 minutes, and the resultant is extracted with chloroform. Then, the extract is dried with magnesium sulfate, filtered, and after removing a solvent therefrom, purified through silica column chromatography to obtain Compound 1g. Herein, a yield is 64%.

$^1$H NMR (500 MHz, CDCl$_3$): δ ppm 7.24 (d, 1H), 7.19 (s, 1H), 7.16 (d, 1H), 7.10 (s, 1H), 7.08 (s, 1H), 6.87 (d, 1H), 6.65 (d, 1H), 4.55 (s, 4H), 4.32 (s, 2H), 2.76 (t, 2H), 1.56 (t, 2H), 1.27 (m, 18H),), 0.87 (t, 3H)

Synthesis of Compound 1 h

Compound 1g (2.52 g, 3.7 mmol) is dissolved in dimethylchloride (200 ml) and then, cooled down to 0° C. Subsequently, diisobutyl aluminum hydride (a 1 M solution in cyclohexane, 8.9 ml, 8.89 mmol) is added thereto, and then, a temperature thereof is slowly increased. After 3 hours, a 5% citric acid solution is added thereto to complete a reaction, and the resultant is extracted with chloroform. Subsequently, the extract is dried with magnesium sulfate, filtered, and after removing a solvent therefrom, purified through silica column chromatography to obtain Compound 1h. Herein, a yield is 42%.

$^1$H NMR (500 MHz, CDCl$_3$): δ ppm 10.08 (s, 1H), 9.99 (s, 1H), 7.53 (s, 1H), 7.42 (d, 1H), 7.17 (d, 1H), 7.07 (s, 1H), 7.03 (s, 1H), 6.85 (d, 1H), 6.65 (d, 1H), 4.78 (s, 2H), 4.76 (s, 2H), 2.76 (t, 2H), 1.65 (t, 2H), 1.29 (m, 18H), 0.87 (t, 3H)

Synthesis of Compound 1

1.0 g of Compound 1h is added to 50 ml of benzene, 4 g of Amberlyst 15 is added thereto, and the obtained mixture is refluxed for 24 hours by connecting a dean-stark apparatus. Then, a solid generated therein is filtered, washed with ethylacetate and dimethylchloride, and dried to obtain Compound 1.

MS (MALDI-TOF-MS, m/z) 650.400 (M+)

Comparative Synthesis Example 1
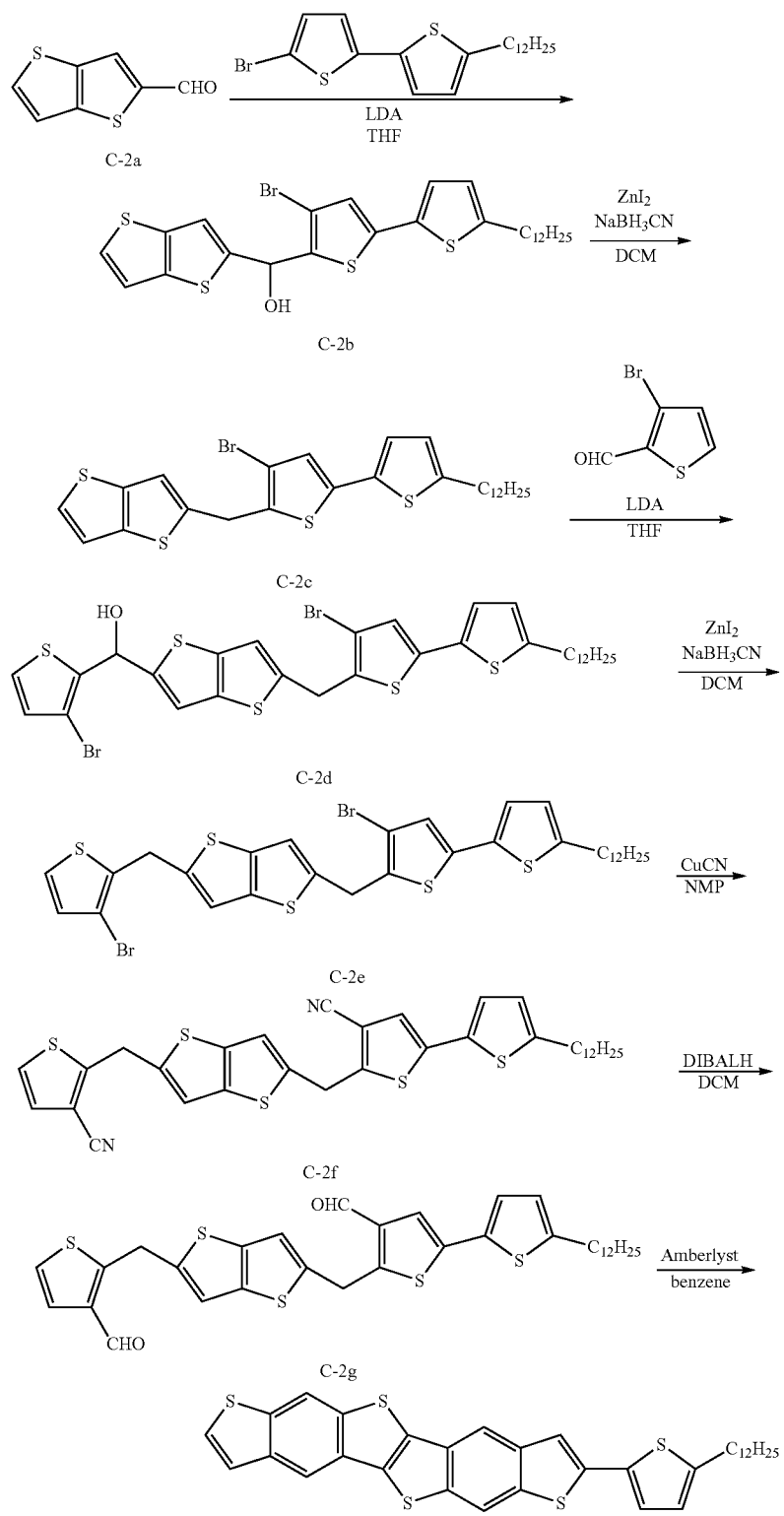

Synthesis of Compound C-2b 5-bromo-5'-dodecyl-2,2'-bithiophene (10 g, 24.18 mmol) is dissolved in 500 ml of tetrahydrofuran (THF) and then, cooled down to −78° C. Subsequently, lithium diisopropylamine (LDA, a 2.0 M solution in THF) (16 ml, 31 mmol) is added thereto and then, stirred for 2 hours, Compound C-2a (4.07 g, 24.18 mmol) is added thereto, and the obtained mixture is slowly heated up to room temperature and stirred for 12 hours. Then, 30 mL of an ammonium chloride saturated solution is added thereto, and the resultant is extracted with ethylacetate and is several times washed with water. Subsequently, the extract is dried with magnesium sulfate, filtered, and after removing a solvent therefrom, purified through silica column chromatography to obtain Compound C-2b. Herein, a yield is 96%.

$^1$H NMR (500 MHz, CDCl$_3$): δ ppm 7.36 (d, 1H), 7.22 (d, 1H), 6.96 (d, 1H), 6.93 (s, 1H), 6.67 (d, 1H), 6.39 (d, 1H), 2.77 (t, 2H), 1.66 (t, 2H), 1.28 (m, 18H), 0.88 (t, 3H)

Synthesis of Compound C-2c

Compound C-2b (13.5 g, 23.2 mmol) is dissolved in dimethylchloride and then, cooled down to 0° C. Subsequently, zinc iodide (ZnI$_2$, 11.8 g, 37.13 mmol) and sodium cyanoborohydride (10.21 g, 162.4 mmol) are added thereto, and the obtained mixture is slowly heated up to room temperature and stirred for 12 hours. Next, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound C-2c. Herein, a yield is 92%.

$^1$H NMR (500 MHz, CDCl$_3$): δ ppm 7.30 (d, 1H), 7.18 (d, 1H), 7.09 (s, 1H), 6.92 (s, 1H), 6.90 (d, 1H), 6.64 (d, 1H), 4.32 (s, 2H), 2.76 (t, 2H), 2.70 (s, 1H), 1.64 (t, 2H), 1.29 (m, 18H),), 0.87 (t, 3H)

Synthesis of Compound C-2d

Compound C-2c (12.1 g, 21.39 mmol) is added to tetrahydrofuran (THF, 500 ml) and then, cooled down to −78° C. Next, lithium diisopropylamine (LDA, 16 ml, 32.08 mmol) is added thereto and then, stirred for 2 hours. Subsequently, 3-bromothiophene-2-carbaldehyde (4.9 g, 25.67 mmol) is dissolved in tetrahydrofuran (THF, 20 ml) and then, stirred for 1 hour. Then, 30 mL of an ammonium chloride saturated solution is added thereto, and an extract therefrom is obtained therefrom with ethylacetate and several times washed with water. Subsequently, the extract is dried with magnesium sulfate, filtered, and after removing a solvent therefrom, purified through silica column chromatography to obtain Compound C-2d. Herein, a yield is 68%.

$^1$H NMR (500 MHz, CDCl$_3$): δ ppm 7.30 (s, 1H), 7.13 (s, 1H), 7.05 (s, 1H), 6.95 (d, 1H), 6.91 (s, 1H), 6.90 (d, 1H), 6.64 (d, 1H), 6.39 (d, 1H), 4.30 (s, 2H), 2.75 (t, 2H), 2.65 (s, 1H), 1.64 (t, 2H), 1.28 (m, 18H), 0.87 (t, 3H)

Synthesis of Compound C-2e

Compound C-2d (11.0 g, 14.54 mmol) is dissolved in dimethylchloride and then, cooled down to 0° C. Subsequently, zinc iodide (ZnI$_2$, 7.4 g, 23.26 mmol) and sodium cyanoborohydride (6.4 g, 101.75 mmol) are added thereto and slowly heated up to room temperature and stirred for 12 hours. Next, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound C-2e. Herein, a yield is 74%.

$^1$H NMR (500 MHz, CDCl$_3$): δ ppm 7.17 (s, 1H), 7.00 (s, 1H), 6.98 (s, 1H), 6.93 (d, 1H), 6.91 (s, 1H), 6.89 (d, 1H), 6.64 (d, 1H), 4.33 (s, 2H), 4.29 (s, 2H), 2.76 (t, 2H), 1.64 (t, 2H), 1.29 (m, 18H), 0.87 (t, 3H)

Synthesis of Compound C-2f

Compound C-2e (7.95 g, 10.73 mmol) is added to 69 ml of N-methyl-2-pyrrolidone, and copper cyanide (CuCN, 3.84 g, 42.93 mmol) is added thereto. The mixture is put in a microwave device and reacted at 180° C. for 2 hours. Subsequently, the resultant is added to a 1 N hydrochloric acid (HCl) solution and then, stirred for 30 minutes, and the resultant is extracted chloroform. Then, the extract is dried with magnesium sulfate, filtered, and after removing a solvent therefrom, purified through silica column chromatography to obtain Compound C-2f. Herein, a yield is 74%.

$^1$H NMR (500 MHz, CDCl$_3$): δ ppm 7.23 (d, 1H), 7.15 (d, 1H), 7.09 (s, 1H), 7.08 (s, 1H), 7.05 (s, 1H), 6.93 (d, 1H), 6.66 (d, 1H), 4.55 (s, 2H), 4.50 (s, 2H), 2.77 (t, 2H), 1.65 (t, 2H), 1.29 (m, 18H), 0.87 (t, 3H)

Synthesis of Compound C-2g

Compound C-2f (5.0 g, 7.9 mmol) is dissolved in 500 ml of dimethylchloride and then, cooled down to 0° C. Next, diisobutyl aluminum hydride (a 1 M solution in cyclohexane, 19 ml, 18.96 mmol) is added thereto, and then, a temperature thereof is slowly increased. After 3 hours, a 5% citric acid solution is added thereto to complete a reaction, and the resultant is extracted with chloroform. Subsequently, the extract is dried with magnesium sulfate, filtered, and after removing a solvent therefrom, purified through silica column chromatography to obtain Compound C-2g. Herein, a yield is 67%.

$^1$H NMR (500 MHz, CDCl$_3$): δ ppm 10.08 (s, 1H), 10.02 (s, 1H), 7.41 (d, 1H), 7.34 (d, 1H), 7.16 (d, 1H), 7.04 (s, 1H), 7.02 (s, 1H), 6.93 (d, 1H), 6.66 (d, 1H), 4.75 (s, 2H), 4.72 (s, 2H), 2.77 (t, 2H), 1.65 (t, 2H), 1.29 (m, 18H), 0.87 (t, 3H)

Synthesis of Compound C-2

3.4 g of Compound C-2g is added to 300 ml of benzene, 12.8 g of Amberlyst15 is added thereto, and the obtained mixture is refluxed for 24 hours by connecting a dean-stark apparatus. Then, a solid generated therein is filtered, washed with ethylacetate and dimethylchloride, and dried to obtain Compound C-2.

MS (MALDI-TOF-MS, m/z) 602.289 (M+)

Comparative Synthesis Example 2

[Reaction Scheme 5]

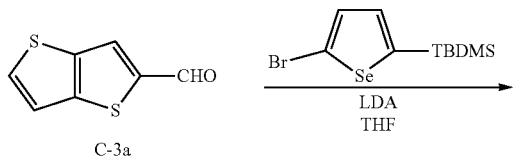

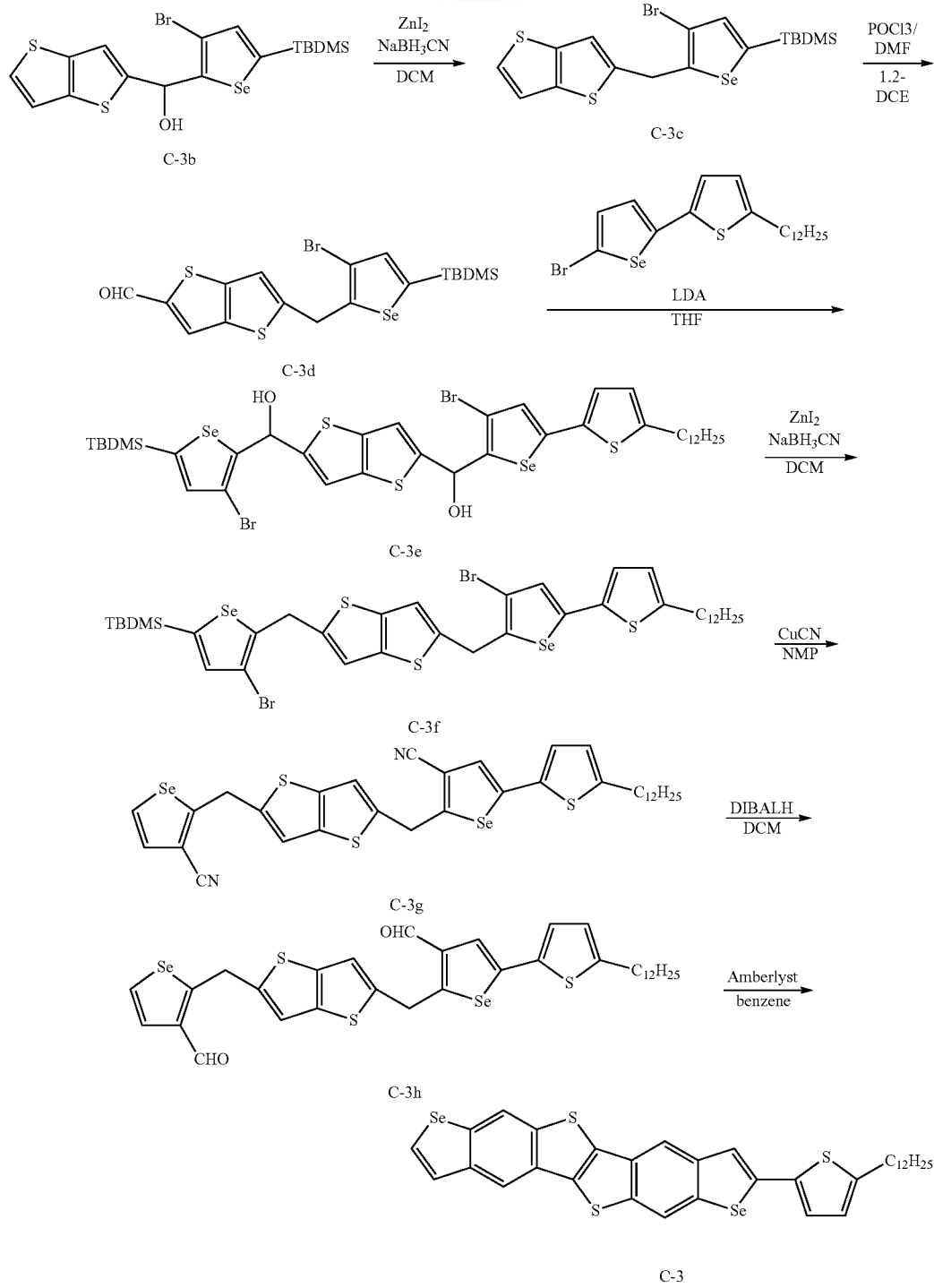

Synthesis of Compound C-3b (5-bromoselenophen-2-yl)(tert-butyl)dimethylsilane (5 g, 15.4 mmol) is dissolved in 200 ml of tetrahydrofuran (THF) and cooled down to −78° C. Then, lithium diisopropylamine (LDA, a 2.0 M solution in THF) (11.57 ml, 23.13 mmol) is added thereto and then, stirred for 2 hours, and Compound 3a (2.16 g, 12.85 mmol) is added thereto, and the obtained mixture is slowly heated up to room temperature and stirred for 12 hours. Subsequently, 30 mL of an ammonium chloride saturated solution is added thereto, and the resultant is extracted with ethylacetate and is several times washed with water. Subsequently, the extract is dried with magnesium sulfate, filtered, and after removing a solvent therefrom, purified through silica column chromatography to obtain Compound C-3b. Herein, a yield is 71%.

$^1$H NMR (500 MHz, CDCl$_3$): δ ppm 7.35 (d, 1H), 7.26 (d, 1H), 7.22 (d, 1H), 6.36 (s, 1H), 2.8 (s, 1H), 0.92 (s, 9H), 0.27 (s, 6H)

Synthesis of Compound C-3c

Compound C-3b (5.4 g, 10.97 mmol) is dissolved in dimethylchloride and then, cooled down to 0° C. Next, zinc iodide (ZnI$_2$, 5.6 g, 17.55 mmol) and sodium cyanoborohydride (4.8 g, 76.76 mmol) are added thereto, and then, slowly heated up to room temperature and stirred for 12 hours. Then, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound C-3c. Herein, a yield is 82%.

$^1$H NMR (500 MHz, CDCl$_3$): δ ppm 7.33 (s, 1H), 7.31 (d, 1H), 7.19 (d, 1H), 7.11 (s, 1H), 4.39 (s, 2H), 0.91 (s, 9H),), 0.24 (s, 6H)

Synthesis of Compound C-3d 1,2-dimethyl formamide (16.25 ml, 209.9 mmol) is put in a 1 L flask and cooled down to 0° C. Subsequently, phosphoryl chloride (9.81 ml, 104.94 mmol) is slowly added thereto, and the obtained mixture is stirred for 2 hours. Then, a solution obtained by dissolving Compound C-3c in 1,2-dichloroethane (250 ml) is added thereto, and the obtained mixture is heated up to 100° C. After 2 hours, a 1N NaOH solution is added thereto to make it basified, and the resultant is extracted with chloroform. Subsequently, the extract is dried with magnesium sulfate, filtered, and after removing a solvent therefrom, purified through silica column chromatography to obtain Compound C-3d. Herein, a yield is 49%.

$^1$H NMR (500 MHz, CDCl$_3$): δ ppm 9.93 (s, 1H), 7.86 (s, 1H), 7.36 (s, 1H), 7.16 (s, 1H), 4.44 (s, 2H), 0.91 (s, 9H),), 0.25 (s, 6H)

Synthesis of Compound C-3e 2-(5-bromoselenophen-2-yl)-5-dodecylthiophene (4.65 g, 0.4 mmol) is dissolved in 300 ml of tetrahydrofuran (THF) and then, cooled down to −78° C. Subsequently, lithium diisopropylamine (LDA, a 2.0 M solution in THF) (7.6 ml, 15.15 mmol) is added thereto and then, stirred for 2 hours, Compound C-3d (5.1 g, 0.4 mmol) is added thereto, and the obtained mixture is slowly heated up to room temperature and stirred for 12 hours. Next, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound C-3e. Herein, a yield is 73%.

$^1$H NMR (500 MHz, CDCl$_3$): δ ppm 7.34 (s, 1H), 7.21 (s, 1H), 7.07 (s, 1H), 7.06 (s, 1H), 6.91 (d, 1H), 6.66 (d, 1H), 6.32 (d, 1H), 4.36 (s, 2H), 2.75 (t, 2H), 1.65 (t, 2H), 1.28 (m, 18H), 0.90 (m, 12H), 0.25 (s, 6H)

Synthesis of Compound C-3f

Compound C-3e (7.1 g, 7.36 mmol) is dissolved in dimethylchloride and then, cooled down to 0° C. Subsequently, zinc iodide (ZnI$_2$, 3.76 g, 11.77 mmol) and sodium cyanoborohydride (3.24 g, 51.51 mmol) are added thereto, and then, the obtained mixture is heated up to room temperature and stirred for 12 hours. Next, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound C-3f. Herein, a yield is 97%.

$^1$H NMR (500 MHz, CDCl$_3$): δ ppm 7.34 (s, 1H), 7.15 (s, 1H), 7.07 (s, 1H), 7.04 (s, 1H), 6.84 (d, 1H), 6.62 (d, 1H), 4.36 (s, 2H), 4.33 (s, 2H), 2.75 (t, 2H), 1.65 (t, 2H), 1.28 (m, 18H), 0.89 (m, 12H), 0.25 (s, 6H)

Synthesis of Compound C-3g

Compound C-3f (6.65 g, 6.98 mmol) is added to 69 ml of N-methyl-2-pyrrolidone, and copper cyanide (CuCN, 2.53 g, 28.06 mmol) is added thereto. Subsequently, the mixture is put in a microwave device and reacted at 180° C. for 2 hours. Subsequently, the resultant is added to a 1 N hydrochloric acid (HCl) solution and then, stirred for 30 minutes, and the resultant is extracted chloroform. Subsequently, the extract is dried with magnesium sulfate, filtered, and after removing a solvent therefrom, purified through silica column chromatography to obtain Compound C-3g. Herein, a yield is 40%.

$^1$H NMR (500 MHz, CDCl$_3$): δ ppm 7.91 (d, 1H), 7.37 (d, 1H), 7.19 (s, 1H), 7.11 (s, 1H), 7.10 (s, 1H), 6.87 (d, 1H), 6.65 (d, 1H), 4.60 (s, 2H), 4.56 (s, 2H), 2.76 (t, 2H), 1.65 (t, 2H), 1.29 (m, 18H), 0.87 (t, 3H)

Synthesis of Compound C-3h

Compound C-3g (3.0 g, 4.1 mmol) is dissolved in 500 ml of dimethylchloride and then, cooled down to 0° C. Subsequently, diisobutylaluminium hydride (a 1 M solution in cyclohexane, 9.9 ml, 9.9 mmol) is added thereto, and a temperature thereof is slowly increased. After 3 hours, a 5% citric acid solution is added thereto to complete a reaction, and the resultant is extracted with chloroform. Then, the extract is dried with magnesium sulfate, filtered, and after removing a solvent therefrom, purified through silica column chromatography to obtain Compound C-3h. Herein, a yield is 33%.

$^1$H NMR (500 MHz, CDCl$_3$): δ ppm 10.04 (s, 1H), 10.00 (s, 1H), 7.83 (d, 1H), 7.68 (d, 1H), 7.53 (s, 1H), 7.06 (d, 1H), 7.02 (s, 1H), 6.85 (d, 1H), 6.66 (d, 1H), 4.83 (s, 2H), 4.79 (s, 2H), 2.76 (t, 2H), 1.65 (t, 2H), 1.29 (m, 18H), 0.87 (t, 3H)

Synthesis of Compound C-3

1.1 g of Compound C-3h is added to 100 ml of benzene, 4.4 g of Amberlyst15 is added thereto, and the obtained mixture is refluxed for 24 hours by connecting a dean-stark apparatus. Subsequently, a solid generated therein is filtered, washed with ethylacetate and dimethylchloride, and dried to obtain Compound C-3.

MS (MALDI-TOF-MS, m/z) 698.197 (M+)

Synthesis Example 2

[Reaction Scheme 6]

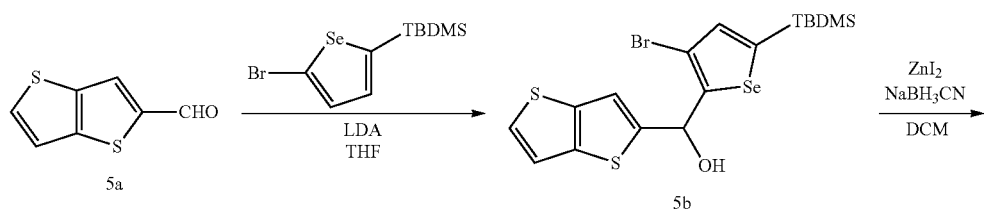

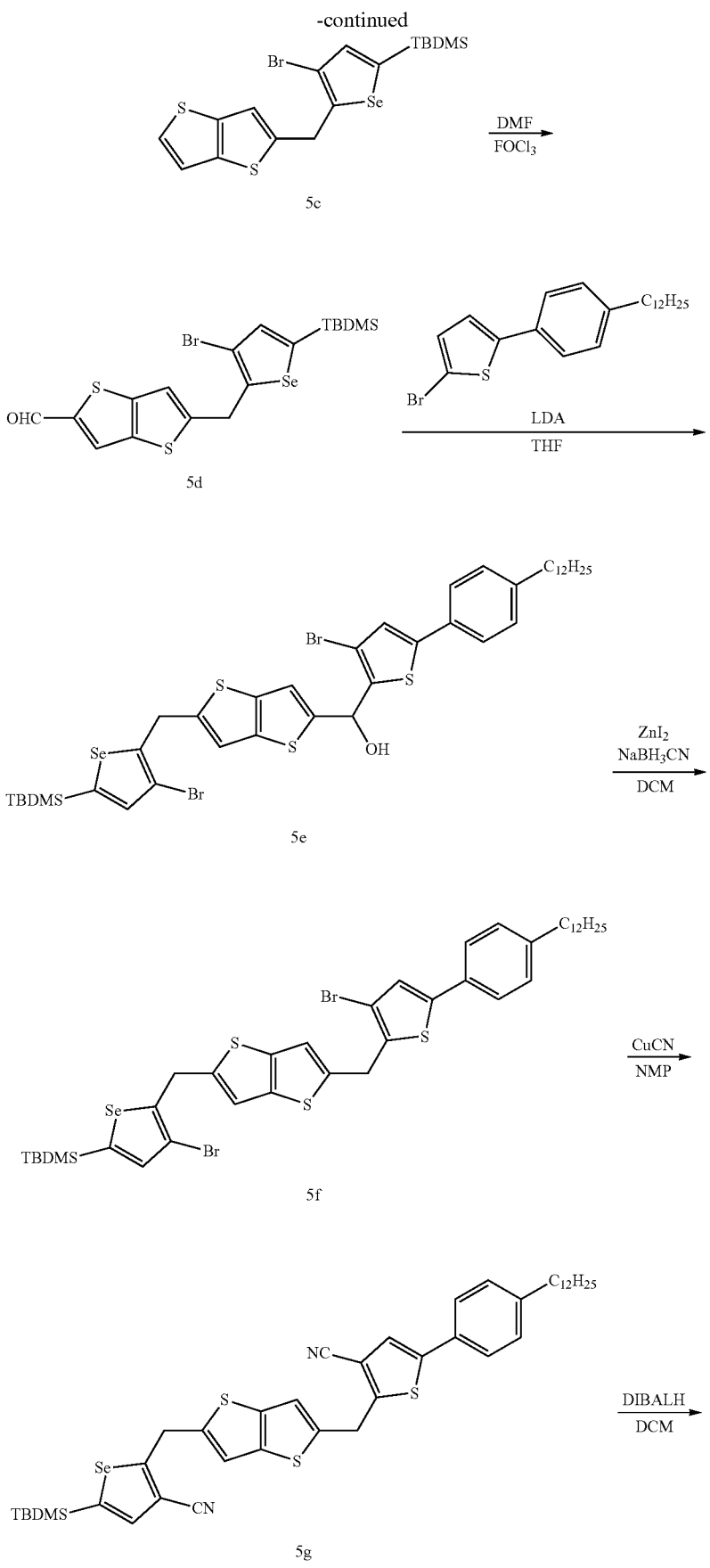

-continued

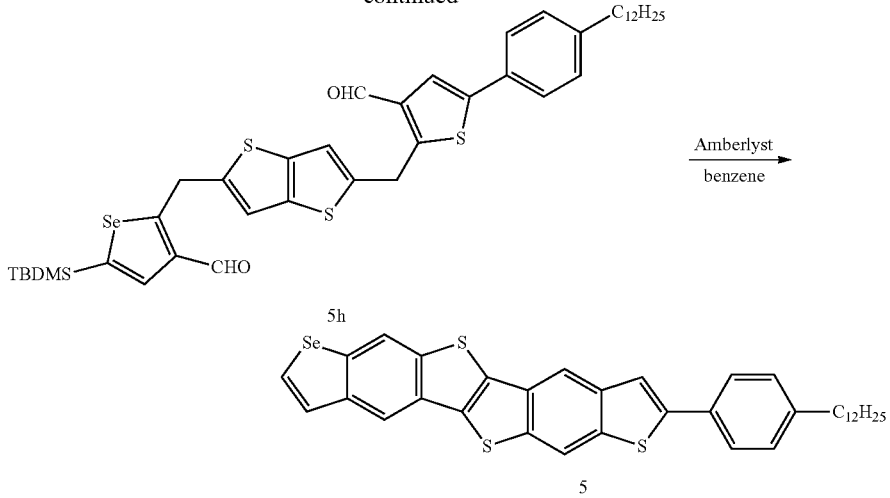

Synthesis of Compound 5b (5-bromoselenophen-2-yl) (tert-butyl)dimethylsilane (5 g, 15.4 mmol) is dissolved in 200 ml of tetrahydrofuran (THF) and then, cooled down to −78° C. Subsequently, lithium diisopropylamine (LDA, a 2.0 M solution in THF) (11.57 ml, 23.13 mmol) is added thereto and then, stirred for 2 hours, Compound 5a (2.16 g, 12.85 mmol) is added thereto, and the obtained mixture is slowly heated up to room temperature and stirred for 12 hours. Next, 30 mL of an ammonium chloride saturated solution is added thereto, and the resultant is extracted with dimethylchloride and is several times washed with water Subsequently, the extract is dried with magnesium sulfate, filtered, and after removing a solvent therefrom, purified through silica column chromatography to obtain Compound 5b. Herein, a yield is 71%.

$^1$H NMR (500 MHz, CDCl$_3$): δ ppm 7.35 (d, 1H), 7.26 (d, 1H), 7.22 (d, 1H), 6.36 (s, 1H), 2.8 (s, 1H), 0.92 (s, 9H), 0.23 (s, 6H)

Synthesis of Compound 5c

Compound 5b (5.4 g, 10.97 mmol) is dissolved in dimethylchloride and cooled down to 0° C. Subsequently, zinc iodide (ZnI$_2$, 5.6 g, 17.55 mmol) and sodium cyanoborohydride (4.8 g, 76.76 mmol) are added thereto, and then, the obtained mixture is slowly heated up to room temperature and stirred for 12 hours. Next, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound 5c. Herein, a yield is 82%.

$^1$H NMR (500 MHz, CDCl$_3$): δ ppm 7.33 (s, 1H), 7.31 (d, 1H), 7.19 (d, 1H), 7.11 (s, 1H), 4.39 (s, 2H), 0.91 (s, 9H),), 0.24 (s, 6H)

Synthesis of Compound 5d 1,2-dimethyl formamide (16.25 ml, 209.9 mmol) is put in a 1 L flask and cooled down to 0° C. Subsequently, phosphoryl chloride (9.81 ml, 104.94 mmol) is slowly added thereto and then, stirred for 2 hours. Next, a solution obtained by dissolving Compound 5c in 1,2-dichloroethane (250 ml) is added thereto, and the obtained mixture is heated up to 100° C. After 2 hours, a 1N sodium hydroxide (NaOH) solution is added thereto to make the solution basified, and the resultant is extracted with chloroform. Subsequently, the extract is dried with magnesium sulfate, filtered, and after removing a solvent therefrom, purified through silica column chromatography to obtain Compound 5d. Herein, a yield is 49%.

$^1$H NMR (500 MHz, CDCl$_3$): δ ppm 9.93 (s, 1H), 7.86 (s, 1H), 7.36 (s, 1H), 7.16 (s, 1H), 4.44 (s, 2H), 0.91 (s, 9H),), 0.25 (s, 6H)

Synthesis of Compound 5e 2-(5-bromothiophen-2-yl)-5-dodecylbenzene (5.25 g, 12.9 mmol) is dissolved in 700 ml of tetrahydrofuran (THF) and then, cooled down to −78° C. Subsequently, lithium diisopropylamine (LDA, a 2.0 M solution in THF) (9.7 ml, 19.3 mmol) is added thereto and then, stirred for 2 hours, Compound 5d (6.5 g, 12.9 mmol) is added thereto, and the obtained mixture is slowly heated up to room temperature and stirred for 12 hours. Next, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound 5e. Herein, a yield is 34%.

$^1$H NMR (500 MHz, CDCl$_3$): δ ppm 7.45 (d, 2H), 7.34 (s, 1H), 7.19 (s, 1H), 7.17 (d, 2H), 7.09 (s, 1H), 7.07 (s, 1H), 6.39 (s, 1H), 4.37 (s, 2H), 2.75 (t, 2H), 2.73 (s, 1H), 1.65 (t, 2H), 1.25 (m, 18H), 0.90 (s, 9H), 0.88 (t, 3H), 0.23 (s, 6H)

Synthesis of Compound 5f

Compound 5e (4.0 g, 4.4 mmol) is dissolved in dimethylchloride and then, cooled down to 0° C. Subsequently, zinc iodide (ZnI$_2$, 2.2 g, 7.0 mmol) and sodium cyanoborohydride (1.9 g, 30.8 mmol) are added thereto, and the obtained mixture is slowly heated up to room temperature and stirred for 12 hours. Next, 30 mL of an ammonium chloride saturated solution is added thereto, and the resultant is extracted with dimethylchloride and is several times washed with water. Subsequently, the extract is dried with magnesium sulfate, filtered, and after removing a solvent therefrom, purified through silica column chromatography to obtain Compound 5e. Herein, a yield is 43%.

$^1$H NMR (500 MHz, CDCl$_3$): δ ppm 7.40 (d, 2H), 7.33 (s, 1H), 7.15 (d, 2H), 7.09 (s, 1H), 7.03 (s, 1H), 7.02 (s, 1H), 4.35 (s, 2H), 4.33 (s, 2H), 2.76 (t, 2H), 1.64 (t, 2H), 1.25 (m, 18H), 0.90 (s, 9H), 0.87 (t, 3H), 0.23 (s, 6H)

Synthesis of Compound 5g

Compound 5f (1.7 g, 1.90 mmol) is added to 30 ml of N-methyl-2-pyrrolidone, and copper cyanide (CuCN, 0.66 g, 7.59 mmol) is added thereto. Then, the mixture is put in a microwave device and then, reacted at 180° C. for 2 hours. Next, the resultant is added to a 1N hydrochloric acid (HCl) solution and then, stirred for 30 minutes, and the resultant is extracted with chloroform. Subsequently, the extract is dried with magnesium sulfate, filtered, and after removing a solvent therefrom, purified through silica column chromatography to obtain Compound 5g. Herein, a yield is 74%.

$^1$H NMR (500 MHz, $CDCl_3$): δ ppm 7.51 (s, 1H), 7.39 (d, 2H), 7.24 (s, 1H), 7.18 (d, 2H), 7.11 (s, 1H), 7.09 (s, 1H), 4.59 (s, 2H), 4.54 (s, 2H), 2.77 (t, 2H), 1.65 (t, 2H), 1.29 (m, 18H), 0.90 (s, 9H), 0.87 (t, 3H), 0.24 (s, 6H)

Synthesis of Compound 5h

Compound 5g (1.0 g, 1.2 mmol) is dissolved in 150 ml of dimethylchloride and then, cooled down to 0° C. Subsequently, diisobutyl aluminum hydride (a 1 M solution in cyclohexane, 3.8 ml, 3.8 mmol) is added thereto, and then, a temperature thereof is slowly increased. After 3 hours, a 5% citric acid solution is added thereto to complete a reaction, and the resultant is extracted with chloroform. Then, the extract is dried with magnesium sulfate, filtered, and after removing a solvent therefrom, purified through silica column chromatography to obtain Compound 5h. Herein, a yield is 80%.

$^1$H NMR (500 MHz, $CDCl_3$): δ ppm 10.08 (s, 1H), 10.07 (s, 1H), 7.85 (s, 1H), 7.54 (s, 1H), 7.43 (d, 2H), 7.18 (d, 2H), 7.07 (s, 1H), 7.06 (s, 1H), 4.81 (s, 2H), 4.76 (s, 2H), 2.77 (t, 2H), 1.65 (t, 2H), 1.25 (m, 18H), 0.90 (s, 9H), 0.87 (t, 3H), 0.25 (s, 6H)

Synthesis of Compound 5

0.86 g of Compound 5h is added to 60 ml of benzene, 1.8 g of Amberlyst 15 is added thereto, and the obtained mixture is refluxed for 24 hours by connecting a dean-stark apparatus. Subsequently, a solid generated therein is filtered, washed with ethylacetate and dimethyl chloride, and dried to obtain Compound 5.

MS (MALDI-TOF-MS, m/z) 644.256 (M+)

Manufacture of Organic Thin Film

Preparation Example 1

An organic thin film having a thickness of 500 Å is manufactured by vacuum evaporation of the compound obtained in Synthesis Example 1 on a silicon wafer covered with 3000 Å-thick $SiO_2$ at a substrate temperature of 170° C.

Comparative Preparation Example 1-1

An organic thin film is formed according to the same method as Preparation Example 1 except that the compound of Comparative Synthesis Example 1 is used instead of the compound of Synthesis Example 1.

Comparative Preparation Example 1-2

An organic thin film is formed according to the same method as Preparation Example 1 except that the compound of Comparative Synthesis Example 2 is used instead of the compound of Synthesis Example 1.

Preparation Example 2

An organic thin film having a thickness of 500 Å is manufactured by vacuum evaporation of the compound obtained in Synthesis Example 2 on a silicon wafer covered with 3000 Å-thick $SiO_2$ at a substrate temperature of 135° C.

Evaluation I

Crystallinity of the organic thin films according to Preparation Examples and Comparative Preparation Examples is confirmed.

The crystallinity is evaluated by comparing a full width at half maximum (FWHM) from an XRD spectrum peak measured with D8 Advance made by Bruker Company.

Figure 2:
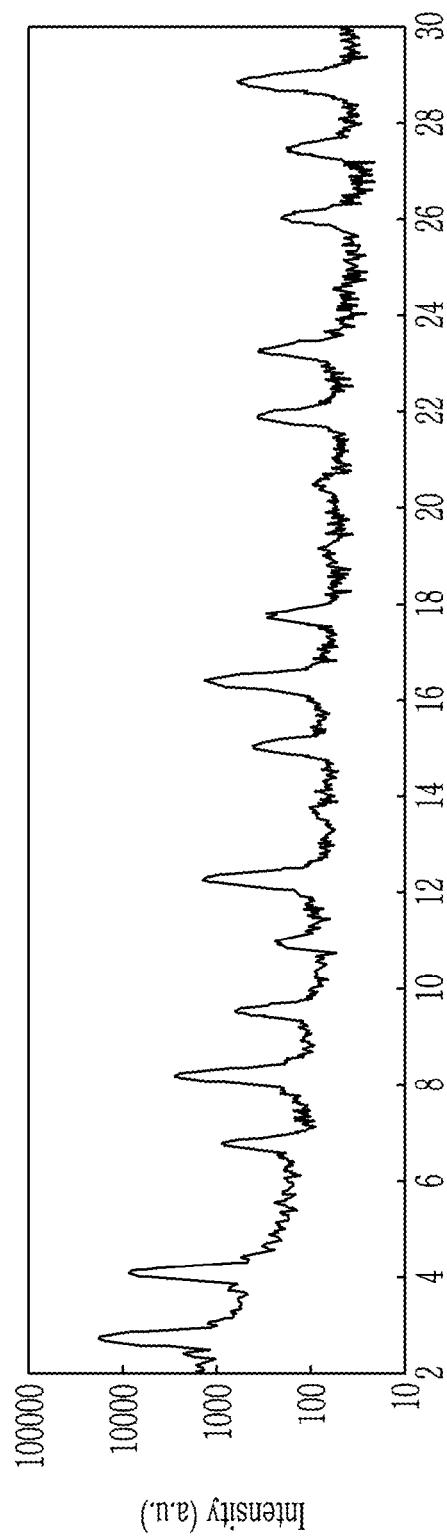
FIG. 2 is a graph showing XRD of the organic thin film according to Preparation Example 1.
Figure 3:
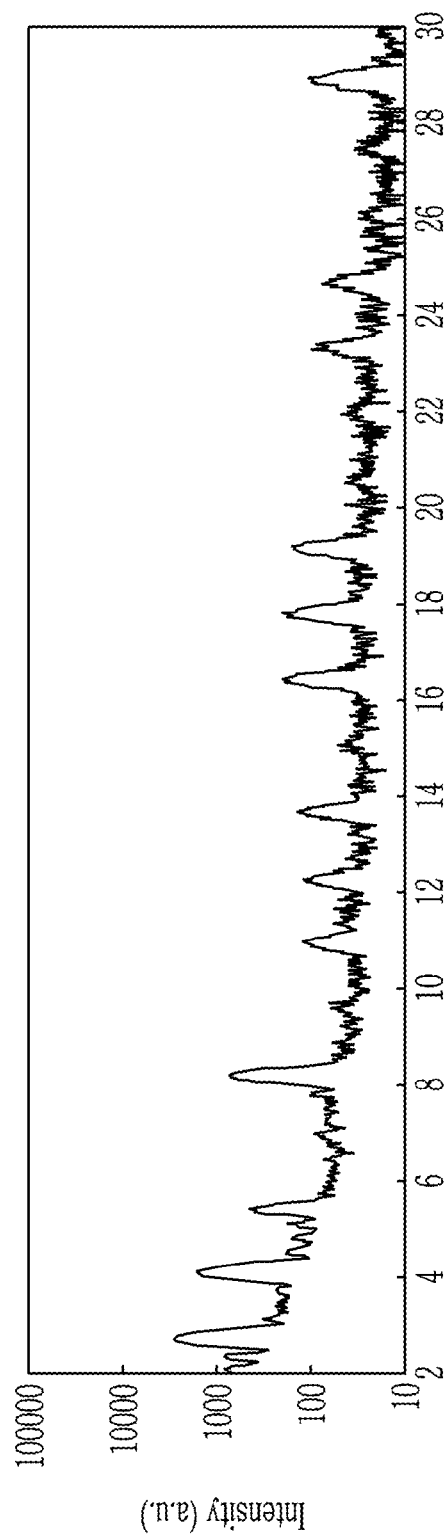
FIG. 3 is a graph showing XRD of the organic thin film according to Comparative Preparation Example 1.
Figure 4:
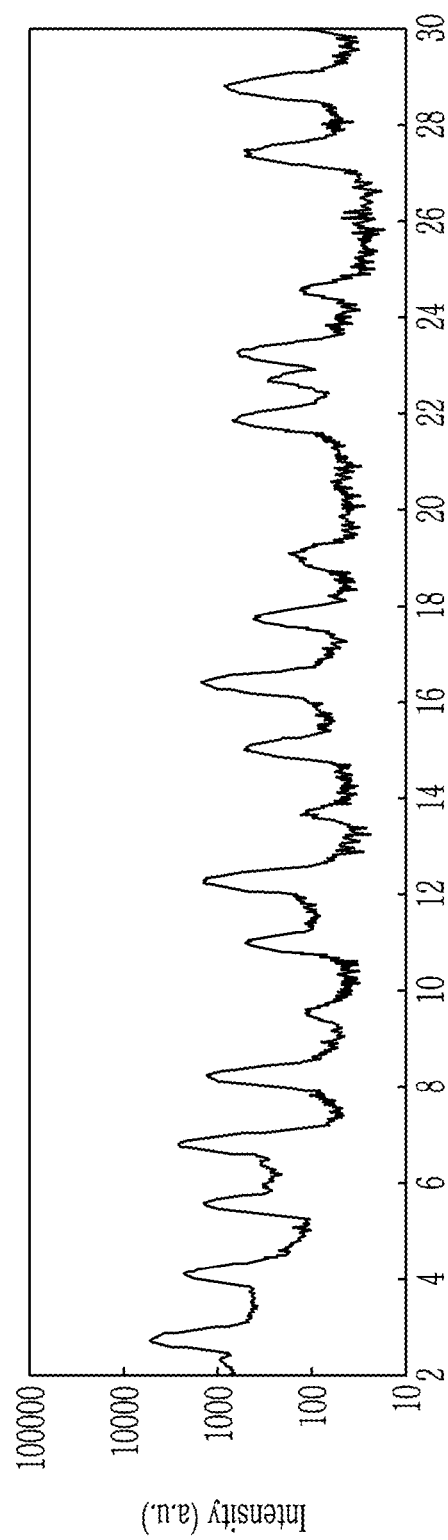
FIG. 4 is a graph showing XRD of the organic thin film according to Preparation Example 2.
Figure 5:
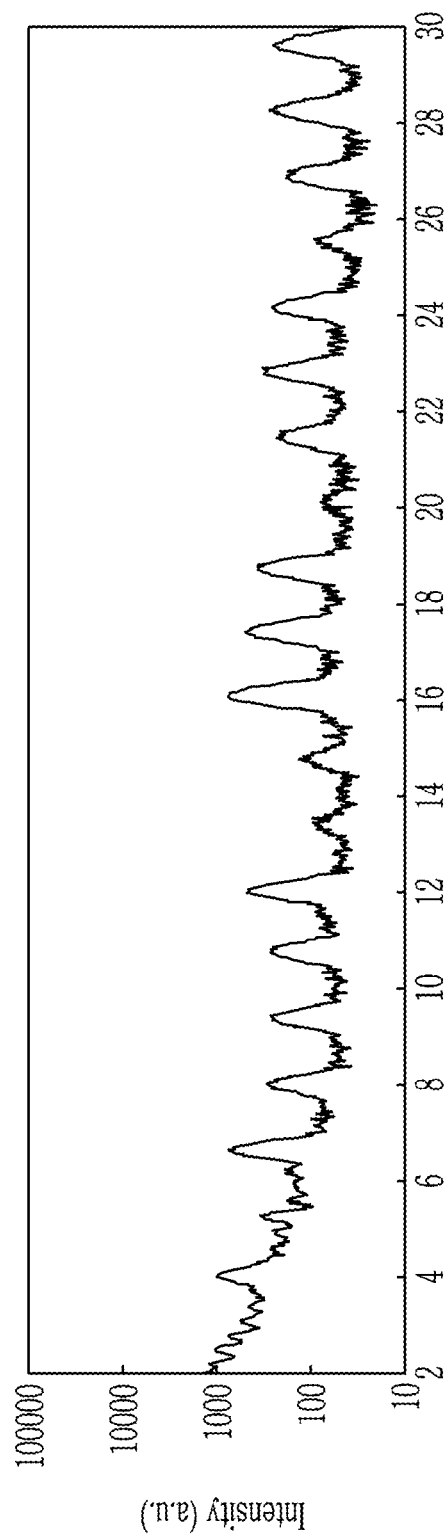
FIG. 5 is a graph showing XRD of the organic thin film according to Comparative Preparation Example 2.

FIG. 2 is a graph showing XRD of the organic thin film according to Preparation Example 1, FIG. 3 is a graph showing XRD of the organic thin film according to Comparative Preparation Example 1-1, FIG. 4 is a graph showing XRD of the organic thin film according to Preparation Example 1-2, and FIG. 5 is a graph showing XRD of the organic thin film according to Preparation Example 2.

Referring to FIGS. 2 to 4, the organic thin film of Preparation Example 1 shows high crystallinity compared with the organic thin films of Comparative Preparation Examples 1-1 and 1-2. Likewise, referring to FIG. 5, the organic thin film of Preparation Example 2 shows high crystallinity. Accordingly, a condensed polycyclic aromatic compound having an asymmetric core structure shows high crystallinity compared with a condensed polycyclic aromatic compound having a symmetric core structure.

Evaluation II

Thermal properties of the organic thin films according to Preparation Examples 1 and 2 are examined.

The thermal properties of the organic thin films are evaluated through TA Instruments Discovery Differential Scanning calorimetry (Discovery DSC).

The results are shown in Table 1.

TABLE 1

|  | Temperature of smetic liquid crystal phase (° C.) |
|---|---|
| Preparation Example 1 | 215° C. |
| Preparation Example 2 | 220° C. |

Referring to Table 1, the organic thin films according to Preparation Examples 1 and 2 have a section where present as a liquid crystal at a desired (and/or alternatively predetermined temperature, and accordingly, a molecular alignment in the liquid crystal phase section may be expected to be improved through a heat treatment.

Manufacture of Thin Film Transistor

Example 1-1

First, a washed silicon wafer substrate coated with $SiO_2$ to be 3000 Å thick is exposed to 02 plasma and then, dipped in an octadecyl trichlorosilane solution diluted in hexane to a concentration of 4 mM to change the surface to be hydrophobic. Subsequently, the compound obtained in Synthesis Example 1 is vacuum-vapor deposited to be 500 Å thick at a substrate temperature of 170° C. to form an organic semiconductor. Then, source and drain electrodes are formed on the organic semiconductor by using a shadow mask and depositing Au to be 1000 Å thick to manufacture a thin film transistor.

Example 1-2

A thin film transistor is manufactured according to the same method as Example 1-1 except that the deposited organic semiconductor is additionally annealed on a hot plate in a nitrogen glove box at 120° C. for 2 hours.

Comparative Example 1-1

A thin film transistor is manufactured according to the same method as Example 1-1 except that the compound obtained in Comparative Synthesis Example 1 is used instead of the compound obtained in Synthesis Example 1.

Comparative Example 1-2

A thin film transistor is manufactured according to the same method as Comparative Example 1-1 except that the deposited organic semiconductor is additionally annealed on a hot plate in a nitrogen glove box at 135° C. for 2 hours.

Comparative Example 2-1

A thin film transistor is manufactured according to the same method as Example 1-1 except that the compound obtained in Comparative Synthesis Example 2 is used instead of the compound obtained in Synthesis Example 1.

Example 2-1

A thin film transistor is manufactured according to the same method as Example 1-1 except that the compound according to Synthesis Example 2 is used instead of the compound according to Synthesis Example 1.

Example 2-2

A thin film transistor is manufactured according to the same method as Example 2-1 except that the deposited organic semiconductor is additionally annealed on a hot plate in a nitrogen glove box at 120° C. for 2 hours.

Evaluation III

Charge mobility of the thin film transistors according to Examples and Comparative Examples is calculated.

The charge mobility of the thin film transistors is obtained by obtaining a graph having $(I_{SD})^{1/2}$ and $V_G$ as variables from a saturation region current equation and a slope in the graph.

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In the equations, $I_{SD}$ is a source-drain current, μ or μFET is charge mobility, $C_O$ is electrostatic capacity of a gate insulating layer, W is a channel width, L is a channel length, $V_G$ is a gate voltage, and $V_T$ is a threshold voltage.

A cut-off leakage current ($I_{off}$) is obtained as a minimum current in an off-state as a current flowing in an off-state. A current on-off ratio ($I_{on}/I_{off}$) is obtained as a ratio of a maximum current in an on-state relative to a minimum current in the off-state.

The results are shown in Tables 2 and 3.

TABLE 2

|  | Charge mobility (cm²/Vs) | Current on-off ratio ($I_{on}/I_{off}$) |
|---|---|---|
| Example 1-1 | 6.86 | 3.0 × 10⁹ |
| Example 1-2 | 8.04 | 8.1 × 10⁸ |
| Comparative Example 1-1 | 5.99 | 1.1 × 10⁷ |
| Comparative Example 1-2 | 4.84 | 1.28 × 10⁸ |
| Comparative Example 2-1 | 3.24 | 5.7 × 10⁸ |

TABLE 3

|  | Charge mobility (cm²/Vs) | Current on-off ratio ($I_{on}/I_{off}$) |
|---|---|---|
| Example 2-1 | 4.98 | 3.5 × 10⁸ |
| Example 2-2 | 6.21 | 2.9 × 10⁸ |

Referring to Tables 2 and 3, the thin film transistors according to Examples exhibit good charge mobility and current on-off ratios. Also, it may be confirmed that charge mobility is further improved by additional annealing the thin film transistors according to Examples. From these results, it may be confirmed that the condensed polycyclic aromatic compound having an asymmetric core structure and an asymmetric substituent structure has good electrical characteristics.

While this disclosure has been described in connection with what is presently considered to be practical example embodiments, it is to be understood that inventive concepts are not limited to the disclosed embodiments, but, on the contrary, inventive concepts are intended to cover various modifications and equivalent arrangements included within the spirit and scope of the appended claims.

What is claimed is:

1. A compound represented by Chemical Formula 1A:

[Chemical Formula 1A]

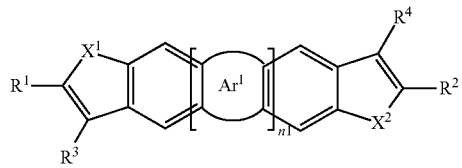

wherein, in Chemical Formula 1A,
X¹ and X² are different from each other and are independently O, S, Se, Te, or NR$^a$,
Ar¹ is at least one substituted or unsubstituted benzene, at least one substituted or unsubstituted furan, at least one substituted or unsubstituted thiophene, at least one substituted or unsubstituted selenophene, at least one substituted or unsubstituted tellurophene, or a structure represented by a substituted or unsubstituted group listed in Group 1:

[Group 1]

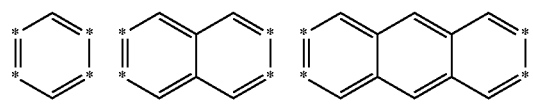

-continued

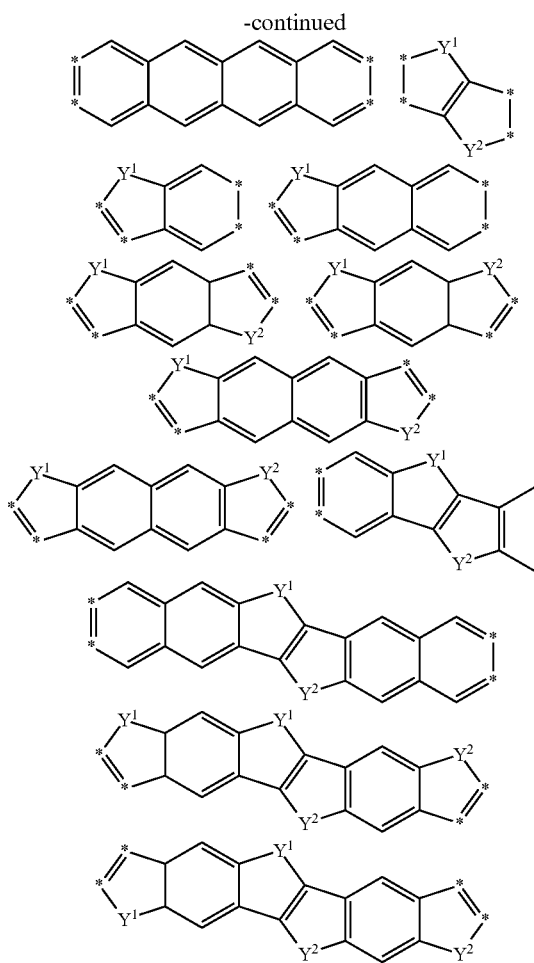

wherein, in Group 1, $Y^1$ and $Y^2$ are independently one of O, S, Se, and Te, and * is a linking point with Chemical Formula 1A $R^1$ and $R^2$ are different from each other or $R^3$ and $R^4$ are different from each other, $R^1$ to $R^4$ and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is 1.

2. The compound of claim 1, wherein one of $X^1$ and $X^2$ is Se or Te.

3. The compound of claim 1, wherein $Ar^1$ includes at least one of a substituted or unsubstituted furan, a substituted or unsubstituted thiophene, substituted or unsubstituted selenophene, and substituted or unsubstituted tellurophene.

4. The compound of claim 1, wherein at least one of $X^1$ and $X^2$ of Chemical Formula 1A is different from $Y^1$ and $Y^2$ listed in Group 1, respectively.

5. The compound of claim 4, wherein one of $X^1$ and $X^2$ is Se or Te, and $Y^1$ and $Y^2$ are independently O or S.

6. The compound of claim 1, wherein one of $R^1$ and $R^2$ is hydrogen, and the other of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

7. The compound of claim 1, wherein one of $R^1$ and $R^2$ is a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and the other of $R^1$ and $R^2$ is a substituted or unsubstituted C4 to C30 branched alkyl group, a substituted or unsubstituted C4 to C30 branched alkenyl group, a substituted or unsubstituted C4 to C30 branched alkynyl group, or a combination thereof.

8. The compound of claim 1, wherein one of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and the other of $R^1$ and $R^2$ is a substituted or unsubstituted C3 to C30 cycloalkyl group, a substituted or unsubstituted C3 to C30 cycloalkenyl group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, or a combination thereof.

9. The compound of claim 1, wherein one of $R^1$ and $R^2$ is a substituted or unsubstituted C3 to C30 cycloalkyl group, a substituted or unsubstituted C3 to C30 cycloalkenyl group, or a substituted or unsubstituted C6 to C30 aryl group, or a combination thereof, and the other of $R^1$ and $R^2$ is a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

10. The compound of claim 1, wherein one of $R^1$ and $R^2$ includes a structure represented by one of Chemical Formulae 2A to 2C:

[Chemical Formula 2A]

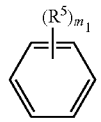

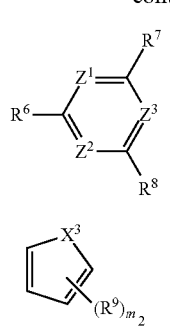

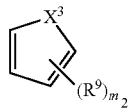

wherein, in Chemical Formula 2A, 2B, or 2C,
$Z^1$ to $Z^3$ are independently N or $CR^b$,
one of $Z^1$ to $Z^3$ is N,
$X^3$ is O, S, Se, Te, $NR^c$, $CR^dR^e$, or $SiR^fR^g$,
m1 is an integer ranging from 0 to 5,
m2 is an integer ranging from 0 to 3,
$R^5$ to $R^9$ and $R^b$ to $R^g$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof or a linking point with Chemical Formula 1A,
when $R^5$ is two or more, each $R^5$ is the same or different and adjacent two $R^5$'s are present independently or linked with each other to form a ring, and
when $R^9$ is two or more, each $R^9$ is the same or different and adjacent two $R^9$'s are present independently or linked with each other to form a ring.

11. The compound of claim 1, wherein
one of $X^1$ and $X^2$ is Se or Te,
one of $R^1$ and $R^2$ is hydrogen, and
the other of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

12. The compound of claim 1, wherein
one of $X^1$ and $X^2$ is Se or Te,
one of $R^1$ and $R^2$ is a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and the other of $R^1$ and $R^2$ is a substituted or unsubstituted C4 to C30 branched alkyl group, a substituted or unsubstituted C4 to C30 branched alkenyl group, a substituted or unsubstituted C4 to C30 branched alkynyl group, or a combination thereof.

13. The compound of claim 1, wherein
one of $X^1$ and $X^2$ is Se or Te,
one of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and
the other of $R^1$ and $R^2$ is a substituted or unsubstituted C3 to C30 cycloalkyl group, a substituted or unsubstituted C3 to C30 cycloalkenyl group, a substituted or unsubstituted C6 to C30 aryl group, a substituted or unsubstituted C3 to C30 cycloheteroalkyl group, a substituted or unsubstituted C3 to C30 cycloheteroalkenyl group, a substituted or unsubstituted C6 to C30 aryloxy group, a substituted or unsubstituted C3 to C30 heteroaryl group, or a combination thereof.

14. The compound of claim 1, wherein
one of $X^1$ and $X^2$ is Se or Te,
one of $R^1$ and $R^2$ is a substituted or unsubstituted C3 to C30 cycloalkyl group, a substituted or unsubstituted C3 to C30 cycloalkenyl group, a substituted or unsubstituted C6 to C30 aryl group, or a combination thereof, and
the other of $R^1$ and $R^2$ is a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

15. An organic thin film comprising:
the compound of claim 1.

16. A thin film transistor comprising
a gate electrode;
a source electrode and a drain electrode; and
an organic semiconductor overlapping with the gate electrode, the source electrode and the drain electrode electrically connected to the organic semiconductor
the organic semiconductor including a compound represented by Chemical Formula 1A:

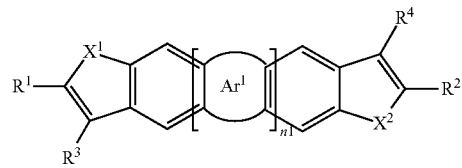

wherein, in Chemical Formulae 1A,
$X^1$ and $X^2$ are different from each other and are independently O, S, Se, Te, or $NR^a$,
$Ar^1$ is at least one substituted or unsubstituted benzene, at least one substituted or unsubstituted furan, at least one substituted or unsubstituted thiophene, at least one substituted or unsubstituted selenophene, at least one substituted or unsubstituted tellurophene, or a structure represented by a substituted or unsubstituted group listed in Group 1:

[Group 1]

wherein, in Group 1, $Y^1$ and $Y^2$ are independently one of O, S, Se, and Te, and * is a linking point with Chemical Formula 1A, $R^1$ and $R^2$ are different from each other or $R^3$ and $R^4$ are different from each other, $R^1$ to $R^4$ and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is 1.

17. The thin film transistor of claim 16, wherein one of $X^1$ and $X^2$ is Se or Te.

18. The thin film transistor of claim 16, wherein $Ar^1$ includes at least one of a substituted or unsubstituted furan, a substituted or unsubstituted thiophene, substituted or unsubstituted selenophene, and substituted or unsubstituted tellurophene.

19. The thin film transistor of claim 16, wherein at least one of $X^1$ and $X^2$ of Chemical Formula 1A is different from $Y^1$ and $Y^2$ listed in Group 1, respectively.

20. The thin film transistor of claim 19, wherein
one of $X^1$ and $X^2$ is Se or Te, and
$Y^1$ and $Y^2$ are independently O or S.

21. The thin film transistor of claim 16, wherein
one of $R^1$ and $R^2$ is hydrogen, and
the other of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

22. The thin film transistor of claim 16, wherein
one of $R^1$ and $R^2$ is a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and
the other of $R^1$ and $R^2$ is a substituted or unsubstituted C4 to C30 branched alkyl group, a substituted or unsubstituted C4 to C30 branched alkenyl group, a substituted or unsubstituted C4 to C30 branched alkynyl group, or a combination thereof.

23. The thin film transistor of claim 16, wherein
one of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and
the other of $R^1$ and $R^2$ is a substituted or unsubstituted C3 to C30 cycloalkyl group, a substituted or unsubstituted C3 to C30 cycloalkenyl group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, or a combination thereof.

24. The thin film transistor of claim 16, wherein
one of $R^1$ and $R^2$ is a substituted or unsubstituted C3 to C30 cycloalkyl group, a substituted or unsubstituted C3 to C30 cycloalkenyl group, a substituted or unsubstituted C6 to C30 aryl group, or a combination thereof, and
the other of $R^1$ and $R^2$ is a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

25. The thin film transistor of claim 16, wherein one of $R^1$ and $R^2$ includes one of Chemical Formulae 2A to 2C:

[Chemical Formula 2A]

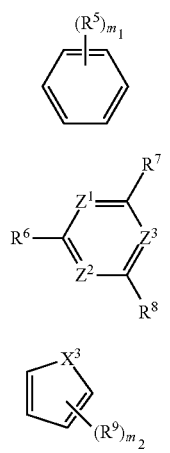

[Chemical Formula 2B]

[Chemical Formula 2C]

wherein, in Chemical Formula 2A, 2B, or 2C,
$Z^1$ to $Z^3$ are independently N or $CR^b$,
one of $Z^1$ to $Z^3$ is N,
$X^3$ is O, S, Se, Te, $NR^c$, $CR^dR^e$, or $SiR^fR^g$,
m1 is an integer ranging from 0 to 5,
m2 is an integer ranging from 0 to 3,
$R^5$ to $R^9$ and $R^b$ to $R^g$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof or a linking point with Chemical Formula 1A,
when $R^5$ is two or more, each $R^5$ is the same or different and adjacent two $R^5$'s are independently present or linked with each other to form a ring, and
when $R^9$ is two or more, each $R^9$ is the same or different and adjacent two $R^9$'s are independently present or linked with each other to form a ring.

26. The thin film transistor of claim 16, wherein
one of $X^1$ and $X^2$ is Se or Te,
one of $R^1$ and $R^2$ is hydrogen, and
the other of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

27. The thin film transistor of claim 16, wherein
one of $X^1$ and $X^2$ is Se or Te,
one of $R^1$ and $R^2$ is a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, and
the other of $R^1$ and $R^2$ is a substituted or unsubstituted C4 to C30 branched alkyl group, a substituted or unsubstituted C4 to C30 branched alkenyl group, a substituted or unsubstituted C4 to C30 branched alkynyl group, or a combination thereof.

28. The thin film transistor of claim 16, wherein
one of $X^1$ and $X^2$ is Se or Te,
one of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and
the other of $R^1$ and $R^2$ is a substituted or unsubstituted C3 to C30 cycloalkyl group, a substituted or unsubstituted C3 to C30 cycloalkenyl group, a substituted or unsubstituted C3 to C30 cycloheteroalkyl group, a substituted or unsubstituted C3 to C30 cycloheteroalkenyl group, a substituted or unsubstituted C6 to C30 aryl group, a substituted or unsubstituted C6 to C30 aryloxy group, a substituted or unsubstituted C3 to C30 heteroaryl group, or a combination thereof.

29. The thin film transistor of claim 16, wherein
one of $X^1$ and $X^2$ is Se or Te,
one of $R^1$ and $R^2$ is a substituted or unsubstituted C3 to C30 cycloalkyl group, a substituted or unsubstituted C3 to C30 cycloalkenyl group, a substituted or unsubstituted C6 to C30 aryl group, or a combination thereof, and
the other of $R^1$ and $R^2$ is a substituted or unsubstituted C3 to C30 cycloheteroalkyl group, a substituted or unsubstituted C3 to C30 cycloheteroalkenyl group, a substituted or unsubstituted C3 to C30 heteroaryl group, or a combination thereof.

30. An electronic device comprising:
the organic thin film of claim 15.

31. An electronic device comprising:
the thin film transistor of claim 16.

* * * * *